United States Patent
Loo et al.

(10) Patent No.: US 9,018,603 B2
(45) Date of Patent: Apr. 28, 2015

(54) PLURIDIRECTIONAL VERY HIGH ELECTRON ENERGY RADIATION THERAPY SYSTEMS AND PROCESSES

(71) Applicant: The Board of Trustees of the Leland Stanford Junior University, Palo Alto, CA (US)

(72) Inventors: Billy Wiseman Loo, Foster City, CA (US); Peter G. Maxim, Palo Alto, CA (US); Valery A. Dolgashev, San Carlos, CA (US)

(73) Assignee: The Board of Trustees of the Leland Stanford Junior University, Palo Alto, CA (US)

(*) Notice: Subject to any disclaimer, the term of this patent is extended or adjusted under 35 U.S.C. 154(b) by 0 days.

(21) Appl. No.: 14/070,376

(22) Filed: Nov. 1, 2013

(65) Prior Publication Data

US 2014/0135563 A1    May 15, 2014

Related U.S. Application Data

(63) Continuation of application No. 13/765,017, filed on Feb. 12, 2013, now Pat. No. 8,618,521.

(60) Provisional application No. 61/606,408, filed on Mar. 3, 2012.

(51) Int. Cl.
   *G21K 5/04*     (2006.01)
   *A61N 5/10*     (2006.01)

(52) U.S. Cl.
   CPC ............ *A61N 5/1064* (2013.01); *A61N 5/1043* (2013.01); *A61N 5/1081* (2013.01); *A61N 2005/1089* (2013.01)

(58) Field of Classification Search
   USPC ......... 250/492.1, 492.3, 423 R, 423 P; 600/1, 600/2, 3, 4, 5
   See application file for complete search history.

(56) References Cited

U.S. PATENT DOCUMENTS

| | | |
|---|---|---|
| 3,757,118 A | 9/1973 | Hodge et al. |
| 4,644,168 A | 2/1987 | Rand et al. |

(Continued)

OTHER PUBLICATIONS

Bazalova, M., et al., "WE-C-BRB-05: Monte Carlo Simulations and Experimental Validation of Rapid Dose Delivery with Very High-Energy Electron Beams"; and Papaconstadopoulos, P., et al., "WE-C-BRB-04: Fast and Accurate Hybrid Source Model for Modulated Electron Radiotherapy"; Medical Physics, vol. 39, No. 6, Jun. 2012, p. 3944.

(Continued)

*Primary Examiner* — Nicole Ippolito
(74) *Attorney, Agent, or Firm* — Kilpatrick Townsend & Stockton LLP; Kenneth R. Shurtz, Esq.

(57) ABSTRACT

A compact high-gradient, very high energy electron (VHEE) accelerator and delivery system (and related processes) capable of treating patients from multiple beam directions with great speed, using all-electromagnetic or radiofrequency deflection steering is provided, that can deliver an entire dose or fraction of high-dose radiation therapy sufficiently fast to freeze physiologic motion, yet with a better degree of dose conformity or sculpting than conventional photon therapy. In addition to the unique physical advantages of extremely rapid radiation delivery, there may also be radiobiological advantages in terms of greater tumor or other target control efficacy for the same physical radiation dose.

74 Claims, 10 Drawing Sheets

(56) References Cited

U.S. PATENT DOCUMENTS

| | | | |
|---|---|---|---|
| 4,737,647 | A | 4/1988 | Stieber |
| 5,452,720 | A | 9/1995 | Smith et al. |
| 5,684,854 | A | 11/1997 | Hughes |
| 6,332,017 | B1 | 12/2001 | Carroll et al. |
| 6,333,966 | B1 | 12/2001 | Schoen |
| 6,459,762 | B1 | 10/2002 | Wong et al. |
| 6,537,052 | B1 | 3/2003 | Adler |
| 6,559,610 | B2 | 5/2003 | Tanaka |
| 6,714,620 | B2 | 3/2004 | Caflisch et al. |
| 6,724,782 | B2 | 4/2004 | Hartemann et al. |
| 6,977,987 | B2 | 12/2005 | Yamashita et al. |
| 7,085,347 | B2 | 8/2006 | Mihara et al. |
| 7,167,540 | B2 | 1/2007 | Muller et al. |
| 7,180,243 | B2 | 2/2007 | Secheresse et al. |
| 7,190,764 | B2 | 3/2007 | Mori et al. |
| 7,206,379 | B2 | 4/2007 | Lemaitre |
| 7,391,850 | B2 | 6/2008 | Kaertner et al. |
| 7,486,775 | B2 | 2/2009 | Forster et al. |
| 7,630,474 | B2 | 12/2009 | Clayton |
| 7,741,624 | B1 | 6/2010 | Sahadevan |
| 7,839,972 | B2 | 11/2010 | Ruchala et al. |
| 8,027,431 | B2 | 9/2011 | Stahl et al. |
| 8,039,819 | B2 | 10/2011 | Faure et al. |
| 8,315,357 | B2 | 11/2012 | Zhu et al. |
| 8,350,226 | B2 | 1/2013 | Zdasiuk et al. |
| 8,405,044 | B2 | 3/2013 | MacKinnon et al. |
| 8,618,521 | B2 * | 12/2013 | Loo et al. ............... 250/492.3 |
| 2002/0191746 | A1 | 12/2002 | Dinsmore |
| 2004/0082855 | A1 | 4/2004 | Robar et al. |
| 2009/0212231 | A1 | 8/2009 | Hill et al. |
| 2009/0252291 | A1 * | 10/2009 | Lu et al. ............... 378/65 |
| 2010/0228116 | A1 | 9/2010 | Lu et al. |
| 2010/0246767 | A1 | 9/2010 | Tanabe |
| 2011/0093243 | A1 | 4/2011 | Tawhai et al. |
| 2012/0262333 | A1 | 10/2012 | Trummer |
| 2012/0326636 | A1 | 12/2012 | Eaton et al. |
| 2013/0016814 | A1 | 1/2013 | Treas et al. |

OTHER PUBLICATIONS

Caryotakis, George, "Development of X-band Klystron Technology at SLAC," Proceedings of the 1997 Particle Accelerator Conference, May 1997, Vancouver, B.C., CA, vol. 3, pp. 2894-2898 (http://www.slac.stanford.edu/cgi-wrap/getdoc/slac-pub-7548.pdf).

DesRosiers, C., et al., "150-250 MeV electron beams in radiation therapy", Physics in Medicine and Biology, vol. 45, No. 7, 2000, pp. 1781-1805.

DesRosiers, Colleen M., "An evaluation of very high energy electron beams (up to 250 MeV) in radiation therapy", Dec. 2004, 163 pages.

Dolgashev Valery et al., "Geometric dependence of radio-frequency breakdown in normal conducting accelerating structures," Applied Physics Letters, 2010, vol. 97, No. 17, (http://apl.aip.org/resource/1/applab/v97/i17/p171501_s1).

Fuchs, T., et al., "Treatment planning for laser-accelerated very-high energy electrons." Physics in Medicine and Biology vol. 54, No. 11, 2009, pp. 3315-3328.

Fuchs, Thomas, "Laser-accelerated particles: Investigations towards applications in radiotherapy", 2007, 152 pages.

Glinec, Yannick, et al., "Radiotherapy with laser-plasma accelerators: Monte Carlo simulation of dose deposited by an experimental quasimonoenergetic electron beam", Medical Physics, vol. 33, No. 1, Jan. 2006, pp. 155-162.

Howell, Rebecca M. et al., "Measurements of secondary neutron dose from 15 MV and 18 MV IMRT," Radiation Protection Dosimetry, 2005; vol. 115, issues 1-4, pp. 508-512, abstract only.

Neilson, Jeffrey et al., "Design of RF feed system and cavities for standing-wave accelerator structure," Nuclear Instruments and Methods in Physics Research A: Accelerators, Spectrometers, Detectors and Associated Equipment, Nov. 2011, vol. 657, issue 1, pp. 52-54, abstract only.

Palowitz, Denise B. et al., "MCNPX 2.7.E Extension," Los Alamos National Laboratory report LA-UR-11-01502, Mar. 2011, draft of later publication Palowitz, Denise B. et al., "MCNPX User's Manual, Version 2.7.0," Los Alamos National Laboratory report LA-CP-11-00438, Apr. 2011, (http://mcnpx.lanl.gov/documents.html).

Schneider, Uwe et al., "Secondary neutron dose during proton therapy using spot scanning," International Journal of Radiation Oncology Biology Physics, 2002, vol. 53, issue 1, pp. 244-251, abstract only.

Tantawi, Sami G., "rf distribution system for a set of standing-wave accelerator structures," Physical Review Special Topics—Accelerators and Beams, 2006, vol. 9, No. 11, pp. 112001-1-112001-6 (http://prst-ab.aps.org/abstract/PRSTAB/v9/i11/e112001).

Walters, B. et al., "DOSXYZnrc Users Manual," Ionizing Radiation Standards National Research Council of Canada, 2011, pp. 1-109, http://irs.inms.nrc.ca/software/beamnrc/documentatio n/pirs794.

Yeboah, C., et al., "Optimization of intensity-modulated very high energy (50-250 MeV) electron therapy", Physics in Medicine and Biology, vol. 47, No. 8, 2002, pp. 1285-1301.

Yeboah, C., et al., "Optimized treatment planning for prostate cancer comparing IMPT, VHEET and 15 MV IMXT", Physics in Medicine and Biology, vol. 47, No. 13, 2002, pp. 2247-2261.

International Search Report and Written Opinion of PCT Application No. PCT/US2013/025765, mailed Apr. 19, 2013, 20 pages.

* cited by examiner

FIG. 2C
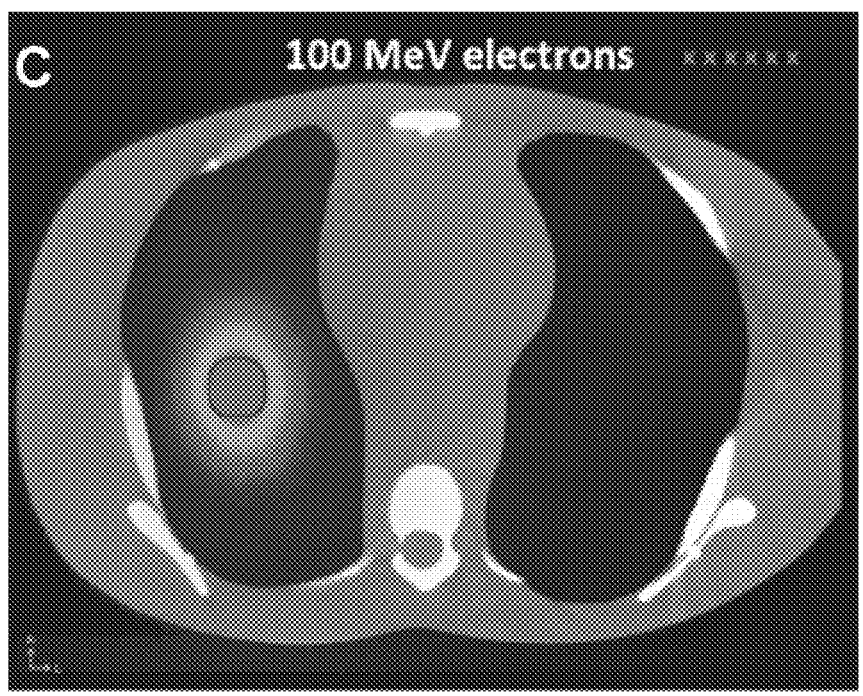
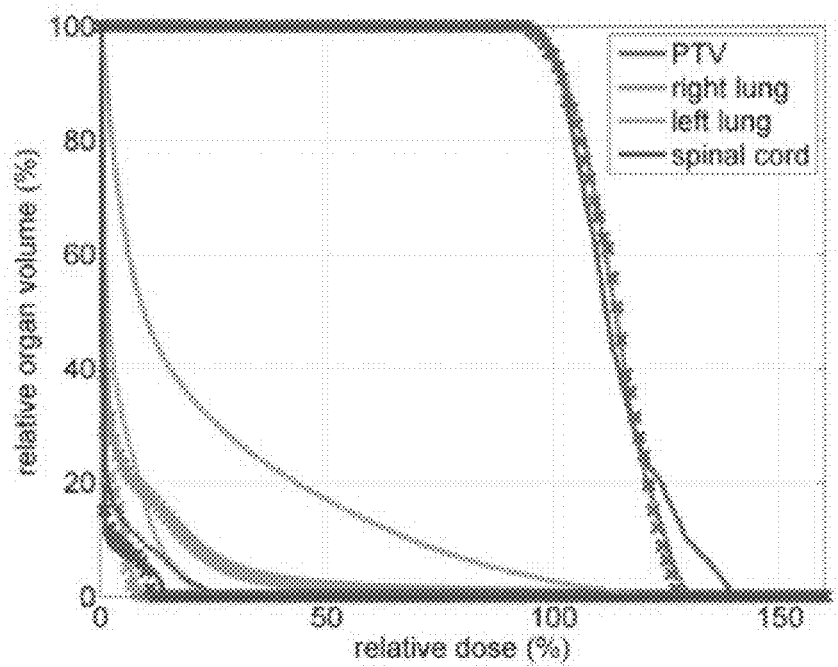
FIG. 2D

FIG. 2E
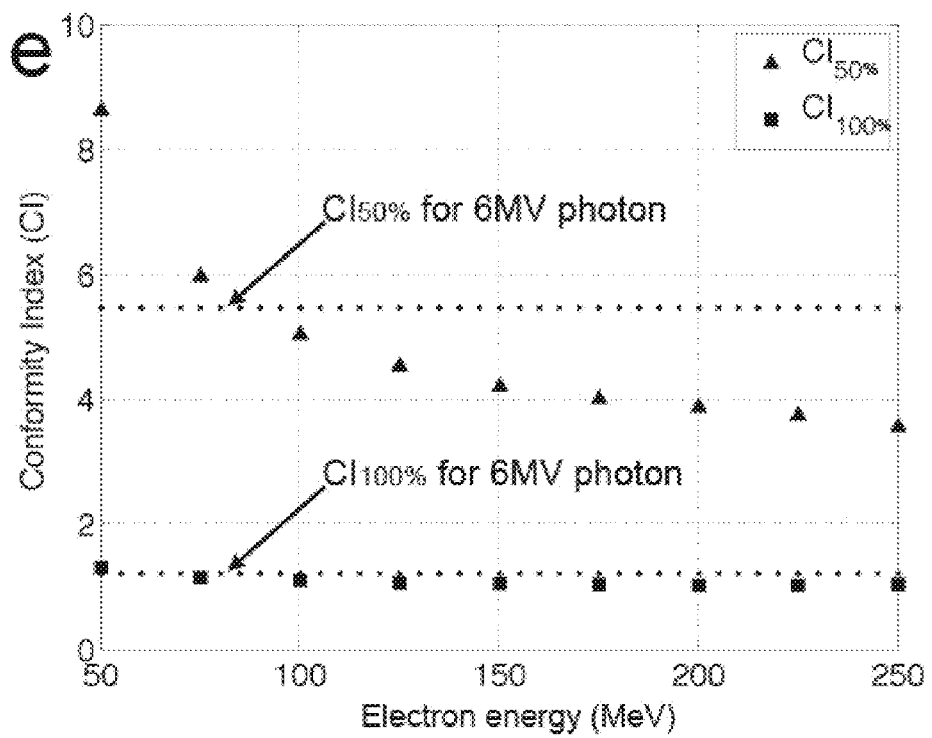
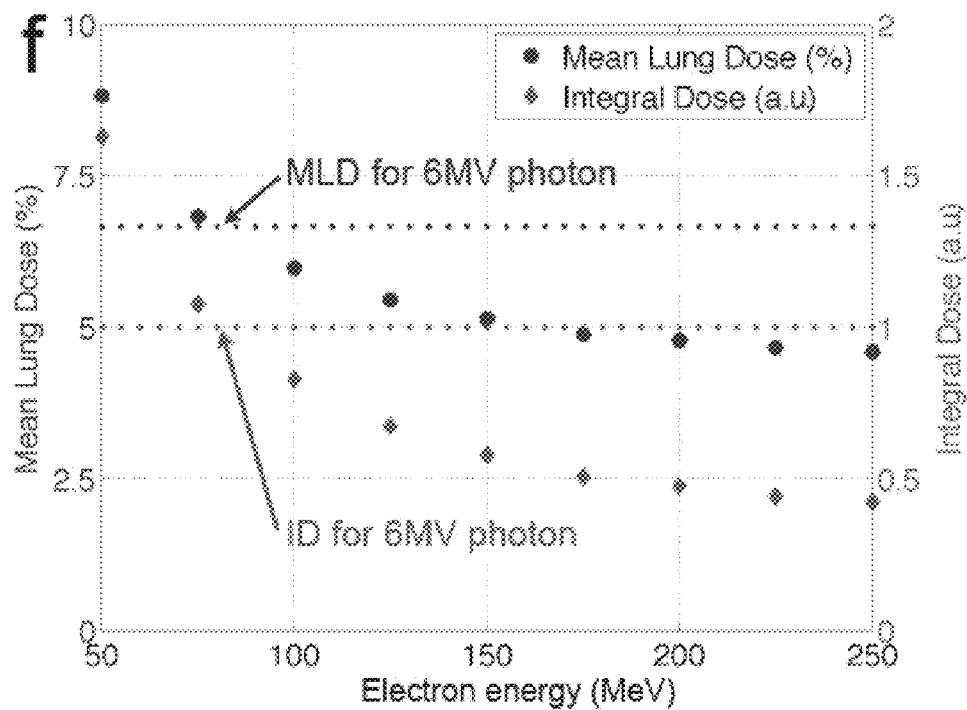
FIG. 2F

PLURIDIRECTIONAL VERY HIGH ELECTRON ENERGY RADIATION THERAPY SYSTEMS AND PROCESSES

CROSS-REFERENCES TO RELATED APPLICATIONS

The present application is a continuation of U.S. application Ser. No. 13/765,017, filed on Feb. 12, 2013, which claims the benefit under 35 USC 119(e) of U.S. Provisional Application No. 61/606,408 filed Mar. 3, 2012; the contents of which are incorporated herein by reference in their entireties.

STATEMENT AS TO RIGHTS TO INVENTIONS MADE UNDER FEDERALLY SPONSORED RESEARCH AND DEVELOPMENT

NOT APPLICABLE

REFERENCE TO A "SEQUENCE LISTING," A TABLE, OR A COMPUTER PROGRAM LISTING APPENDIX SUBMITTED ON A COMPACT DISK

NOT APPLICABLE

FIELD OF THE INVENTION

The invention generally relates to radiation therapy and more particularly to systems and methods for very high electron energy radiation therapy.

BACKGROUND OF THE INVENTION

Major technical advances in radiation therapy in the past two decades have provided effective sculpting of 3-D dose distributions and spatially accurate dose delivery by imaging verification. These technologies, including intensity modulated radiation therapy (IMRT), hadron therapy, and image guided radiation therapy (IGRT) have translated clinically to decreased normal tissue toxicity for the same tumor control, and more recently, focused dose intensification to achieve high local control without increased toxicity, as in stereotactic ablative radiotherapy (SABR) and stereotactic body radiotherapy (SBRT).

One key remaining barrier to precise, accurate, highly conformal radiation therapy is patient, target and organ motion from many sources including musculoskeletal, breathing, cardiac, organ filling, peristalsis, etc. that occurs during treatment delivery, currently 15-90 minutes per fraction for state-of-the-art high-dose radiotherapy. As such, significant effort has been devoted to developing "motion management" strategies, e.g., complex immobilization, marker implantation, respiratory gating, and dynamic tumor tracking.

BRIEF SUMMARY OF THE INVENTION

A fundamentally different approach to managing motion is to deliver the treatment so rapidly that no significant physiologic motion occurs between verification imaging and completion of treatment. According to certain embodiments of the invention, an accelerator, more preferably a compact high-gradient, very high energy electron (VHEE) linear accelerator, which may be a standing wave linear accelerator, together with a delivery system capable of treating patients from multiple beam directions, potentially using all-electro-magnetic or radiofrequency deflection steering is provided, that can deliver an entire dose or fraction of high-dose (e.g., 20-30 Gy) radiation therapy sufficiently fast to freeze physiologic motion, yet with a better degree of dose conformity or sculpting than conventional photon therapy. The term. "sufficiently fast to freeze physiologic motion" in this document means preferably faster than one human breath hold, more preferably less than 10 seconds, even more preferably less than 5 seconds, even more preferably less than one heartbeat and most preferably less than a second. In addition to the unique physical advantages of extremely rapid radiation delivery, there may also be radiobiological advantages in terms of greater tumor control efficacy for the same physical radiation dose. Certain embodiments of the invention can also treat non-tumor targets, such as, by way of nonlimiting example, ablation or other treatment of: (1) nerves or facet joints for pain control; (2) foci in the brain for neuromodulation of neurologic conditions including pain, severe depression, and seizures; (3) portions of the lung with severe emphysema; and/or (4) abnormal conductive pathways in the heart to control refractory arrhythmias.

According to certain embodiments of the invention, there is provided a system for delivering very high electron energy beam to a target in a patient, comprising:
  An accelerator capable of generating a very high electron energy beam;
  A beam steering device capable of receiving the beam from the accelerator and steering the beam to the target from multiple directions; and
  A controller capable of controlling length of time that the beam irradiates the target, the length of time sufficiently fast to freeze physiologic motion, and to control the directions in which the beam steering device steers the beam to the target.

According to some embodiments, the controller is configured to receive information from an imaging device and use the information from the imaging device to control the directions in which the beam steering device steers the beam to the target.

According to some embodiments, the accelerator is a linear accelerator capable of generating a beam having energy of between 1 and 250 Mev, more preferably 50 and 250 MeV and most preferably between 75 and 100 MeV.

According to some embodiments, the time period is preferably faster than one human breath hold, more preferably less than 10 seconds, even more preferably less than 5 seconds, even more preferably less than one heartbeat and most preferably less than a second.

According to some embodiments, the beam steering device is an electro-magnetic device.

According to some embodiments, the beam steering device is a radiofrequency deflector device.

According to some embodiments, the beam steering device includes a gantry, the gantry including multiple beam ports.

According to some embodiments, the beam steering device includes a continuous annular gantry.

According to some embodiments, the beam steering device is capable of providing thin pencil beam raster scanning.

According to some embodiments, the beam steering system is capable of providing volume filling scanning.

According to some embodiments, the beam steering device includes no mechanical moving parts.

According to other embodiments, there is provided a system for delivering very high electron energy beam to a target in a patient, comprising:
  An accelerator capable of generating a very high electron energy beam;

A beam steering device capable of receiving the beam from the accelerator and steering the beam to the target from multiple directions;

A controller capable of controlling length of time that the beam irradiates the target, the length of time sufficiently fast to freeze physiologic motion, and to control the directions in which the beam steering device steers the beam to the target; and An imaging device capable of generating images of the target and providing information from the imaging device to the controller to control the directions in which the beam steering device steers the beam to the target.

According to some embodiments, the imaging device is capable of providing information to the controller to trigger when the system delivers the beam to the target.

According to some embodiments, using information from the imaging device, the system is capable of automatically delivering the beam to the target from multiple predetermined directions at multiple predetermined points in time.

According to some embodiments, the accelerator is a linear accelerator capable of generating a beam having energy of between 1 and 250 Mev, more preferably 50 and 250 MeV and most preferably between 75 and 100 MeV.

According to some embodiments, the time period is preferably faster than one human breath hold, more preferably less than 10 seconds, even more preferably less than 5 seconds, even more preferably less than one heartbeat and most preferably less than a second.

According to some embodiments, the beam steering device is an electro-magnetic device.

According to some embodiments, the beam steering device is a radiofrequency deflector device.

According to some embodiments, the beam steering device includes no mechanical moving parts.

According to other embodiments, there is provided a method for delivering a beam of very high electron energy to a target in a patient, comprising:

Providing a system for delivering very high electron energy beam to a target in a patient, the system comprising:

An accelerator capable of generating a very high electron energy beam;

A beam steering device capable of receiving the beam from the accelerator and steering the beam to the target from multiple directions; and A controller capable of controlling length of time that the beam irradiates the target, the length of time sufficiently fast to freeze physiologic motion, and to control the directions in which the beam steering device steers the beam to the target; and Actuating the system to cause it to deliver the beam to the target.

According to some embodiments, providing the system includes providing an accelerator that is capable of generating a beam having energy of between 1 and 250 Mev, more preferably 50 and 250 MeV and most preferably between 75 and 100 MeV.

According to some embodiments, providing the system includes providing a controller capable of controlling length of time that the beam irradiates the target, the time period preferably faster than one human breath hold, more preferably less than 10 seconds, even more preferably less than 5 seconds, even more preferably less than one heartbeat and most preferably less than a second.

According to some embodiments, providing the system includes providing a beam steering device that is an electro-magnetic device.

According to some embodiments, providing the system includes providing a beam steering device that is a radiofrequency deflector device.

According to some embodiments, providing the system includes providing a beam steering device that includes no mechanical moving parts.

According to some embodiments, there is further provided a controller that is configured to receive information from an imaging device and use the information from the imaging device to control the directions in which the beam steering device steers the beam to the target.

According to some embodiments, there is further provided an imaging device capable of generating images of the target and providing information from the imaging device to the controller to control the directions in which the beam steering device steers the beam to the target.

According to some embodiments, providing the imaging device includes providing an imaging device that is capable of providing information to the controller to trigger when the system delivers the beam to the target.

According to some embodiments, providing the imaging device includes providing an imaging device wherein, using information from the imaging device, the system is capable of automatically delivering the beam to the target from multiple predetermined directions at multiple predetermined points in time.

According to other embodiments, there is also provided a system for delivering a transverse-modulated electron beam to a target in a patient, comprising:

A photoelectron gun configured to generate a transverse-modulated electron beam from an optical image produced by a light source such as a laser and projected on a photocathode;

An accelerator capable of increasing the energy level of the transverse-modulated electron beam to a predetermined level;

A beam steering device capable of receiving the transverse-modulated electron beam from the accelerator and steering the transverse-modulated electron beam to the target from multiple directions; and A controller capable of controlling length of time that the transverse-modulated electron beam irradiates the target, the length of time sufficiently fast to freeze physiologic motion, and to control the directions in which the beam steering device steers the transverse-modulated electron beam to the target.

DETAILED DESCRIPTION OF THE INVENTION

A. Significance

Figure 1:
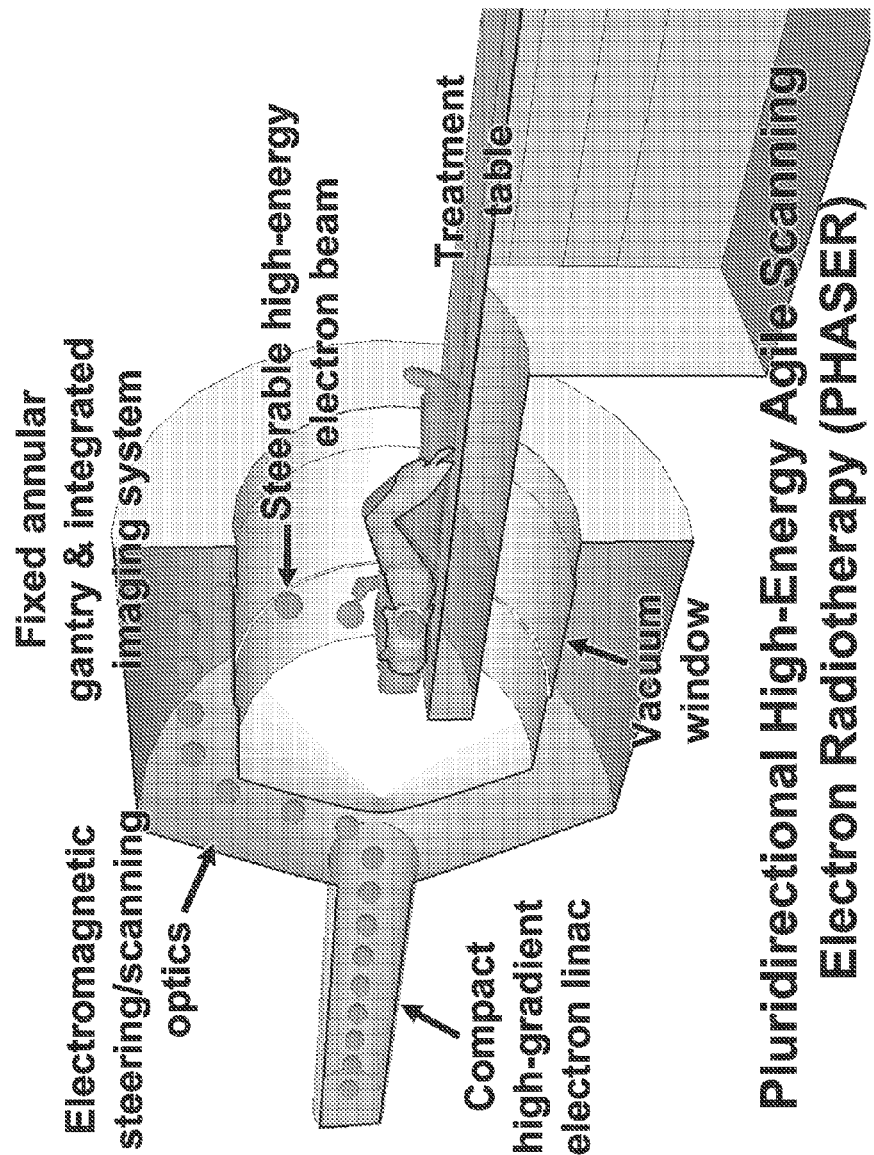
FIG. 1 is a schematic representation of one embodiment of the invention, showing beam access from a large number of axial directions by electromagnetic- or radiofrequency deflection steering.

In the U.S., cancer has surpassed heart disease as the leading cause of death in adults under age 85, and of the 1.5 million patients diagnosed with cancer each year, about two thirds will benefit from radiation therapy (RT) at some point in their treatment, with nearly three quarters of those receiving RT with curative intent. Worldwide, the global burden of cancer is increasing dramatically owing to the aging demographic, with an incidence of nearly 13 million per year and a projected 60% increase over the next 20 years, and the number of patients who could benefit from RT far exceeds its availability. Moreover, even when RT is administered with curative intent, tumor recurrence within the local radiation field is a major component of treatment failure for many common cancers. Thus, improvements in the efficacy of and access to RT have tremendous potential to save innumerable lives.

Although there have been major technological advances in radiation therapy in recent years, a fundamental remaining barrier to precise, accurate, highly conformal radiation therapy is patient, target, and organ motion from many sources including musculoskeletal, breathing, cardiac, organ filling, peristalsis, etc. that occurs during treatment delivery. Conventional radiation delivery times are long relative to the time scale for physiologic motion, and in fact, more sophisticated techniques tend to prolong the delivery time, currently 15-90 minutes per fraction for state-of-the-art high-dose radiotherapy. The very fastest available photon technique (arc delivery with flattening filter free mode) requires a minimum of 2-5 min to deliver 25 Gy. Significant motion can occur during these times.

Even for organs unaffected by respiratory motion, e.g., the prostate, the magnitude of intrafraction motion increases significantly with treatment duration, with 10% and 30% of treatments having prostate displacements of >5 mm and >3 mm, respectively, by only 10 minutes elapsed time. As such, considerable effort has been devoted to developing "motion management" strategies in order to suppress, control, or compensate for motion. These include complex immobilization, fiducial marker implantation, respiratory gating, and dynamic tumor tracking, and in all cases still require expansion of the target volume to avoid missing or undertreating the tumor owing to residual motion, at the cost of increased normal tissue irradiation.

Several factors contribute to long delivery times in existing photon therapy systems. First, production of x-rays by Bremsstrahlung is inefficient, with less than 1% of the energy of the original electron beam being converted to useful radiation. Second, collimation, and particularly intensity modulation by collimation, is similarly inefficient as the large majority of the beam energy is blocked by collimation. Third, using multiple beam angles or arcs to achieve conformal dose distributions requires mechanical gantry motion, which is slow. Treatment using protons or other heavier ions has dosimetric advantages over photon therapy, and these particles can be electromagnetically scanned very rapidly across a given treatment field. However changing beam directions still requires mechanical rotation of the massive gantry, which is much larger and slower than for photon systems. The cost and size of these systems also greatly limits their accessibility.

Very high-energy electrons (VHEE) in the energy range of 50-250 MeV have shown favorable dose deposition properties intermediate between megavoltage (MV) photons and high-energy protons. Without the need for inefficient Bremsstrahlung conversion or physical collimation, and with a smaller steering radius than heavier charged particles, treatment can be multiple orders of magnitude faster than any existing technology in a form factor comparable to conventional medical linacs. According to certain embodiments of the invention, a compact high-gradient VHEE accelerator and delivery system is provided that is capable of treating patients from multiple beam directions with great speed, using electro-magnetic, radiofrequency deflection or other beam steering devices. Such embodiments may deliver an entire dose or fraction of high-dose radiation therapy sufficiently fast to freeze physiologic motion, yet with a better degree of dose conformity or sculpting, and decreased integral dose and consequently decreased risk of late toxicities and secondary malignancies, than the best MV photon therapy. Suitable energy ranges in accordance with certain embodiments of the invention are 1-250 MeV, more preferably 50-250 MeV, and most preferably 75-100 MeV. Again, as described in the Summary section above, the term "sufficiently fast to freeze physiologic motion" in this document means preferably faster than one human breath hold, more preferably less than 10 seconds, even more preferably less than 5 seconds, even more preferably less than one heartbeat and most preferably less than a second.

According to some embodiments, a major technological advance is extremely rapid or near instantaneous delivery of high dose radiotherapy that can eliminate the impact of target motion during RT, affording improved accuracy and dose conformity and potentially radiobiological effectiveness that will lead to improved clinical outcomes. Rapid imaging and treatment can also lead to greater clinical efficiency and patient throughput. For standard treatments, the room occupancy time can be reduced to less than 5 minutes. There can also be a great practical advantage for special populations like pediatric patients who normally require general anesthesia for adequate immobilization during long treatments, and who can instead be treated with only moderate sedation for such rapid treatments. Such advantages can be achieved, according to some embodiments, in a compact physical form factor and low cost comparable to conventional photon therapy systems, and much lower than hadron therapy systems. One embodiment is shown in FIG. 1, which shows a system wherein beam access from a large number of axial directions is achieved by electromagnetic steering without moving parts or with a minimum of moving parts, for extremely fast highly conformal radiotherapy. The system shown in FIG. 1 includes a compact linear accelerator, a beam steering device, and a controller for controlling the very high electron energy beam that is delivered to the patient. The embodiment can also include an integrated imaging device that obtains images of portions of the patient including the tumor or other site to be treated. The imaging device can also provide information to allow for control of the beam steering device in order to control directions from which the beam is delivered, and timing of the beam, among other variables.

Furthermore, the prolonged treatment times of conventional highly conformal RT are sufficiently long for repair of sublethal chromosomal damage to occur during treatment, potentially reducing the tumoricidal effect of the radiation dose. Thus in addition to the unique physical advantages of extremely rapid radiation delivery, there may also be dose advantages. It is hypothesized that the treatment times sufficiently fast to freeze physiologic motion that are made possible by certain embodiments of the invention may be more biologically effective, producing enhanced tumor cell killing for the same physical dose. Differences between certain embodiments of the invention and conventional photon therapy that impact biological effectiveness include a much faster delivery time and differences in the radiation quality.

Dose rate effects are well described in the radiobiology literature, in which prolongation of delivery times results in decreased cell killing. The main mechanism known to be responsible for this effect is repair of potentially lethal DNA double strand breaks (DSB) during the interval over which a given dose of radiation is delivered. Several in vitro studies have demonstrated significantly decreased cell killing when delivery is protracted from a few minutes to tens of minutes. However, there is a lack of consensus in the literature regarding the kinetics of sublethal damage (SLD) repair, with some studies suggesting that components of SLD repair may have repair half-times of as little as a few minutes. If so, shortening the delivery times even from a few minutes to a time period sufficiently fast to freeze physiologic motion has the potential to increase tumor cell killing.

B. Beam Steering

Some embodiments of the invention take advantage of the fact that electrons are relatively easier to manipulate using electric and magnetic fields. Charged particles such as electrons and protons can be produced as spatially coherent beams that can be steered electromagnetically or with radiofrequency deflection with high rapidity. Thus, direct treatment with scanned charged particle beams can eliminate the inefficiencies of Bremsstrahlung photon multiple beams from different directions toward the target in the patient. All conventional radiation therapy systems accomplish multidirectional treatment by mechanically rotating a gantry, or an entire compact linac, or even cyclotron, directing radiation to the target from one direction at a time.

As a preliminary matter, at the end of the accelerator structure the beam must be deflected and then transported to the exit port and toward a target in or on the patient, such as a tumor in the patient. At the exit port the beam must be steered again to change the exit angle and/or beam size to adapt to the treatment plan. Electro-magnetic and/or RF deflector steering systems will manipulate the electron beam.

A variety of gantry designs are potentially available, from simple to complex, ranging from multiple discrete beam ports arranged around the patient to a continuous annular gantry to allow arbitrary incident axial beam angles. The design depends on a number of factors, including scanning strategies such as thin pencil beam raster scanning vs. volume filling with non-isocentric variable-size shots, or use of transverse modulation of the electron beam profile.

According to one embodiment, the steering system of the electron beam starts at the end of the accelerator structure with a two-dimensional deflector, which guides the beam into one of multiple channels. Once the beam enters a specific channel it is guided all the way to the exit of the channel, which is perpendicular to the axis of the patient. The guidance through the channels is achieved using low aberration electron optics. At the exit of each channel another small 2-D deflector can be added to scan the beam over a target. The number of channels can then be about 10-50. For a given channel width, a larger initial deflection would increase the number of channel entry ports that fit into the circumference swept by the beam. Thus if the field strength were increased, the number of channels could be increased to 100 or more.

Because a linear accelerator will typically consume 50 to 100 MW of peak power to achieve 100 MeV of acceleration, over a length of 2 to 1 m respectively, potential RF deflectors can be considered. These have the advantage of being ultra-fast and permit capitalization on the RF infrastructure that is used for the main accelerator structure. In any event, the delivery system is preferably optimized to achieve high-dose treatment times sufficiently fast to freeze physiologic motion.

Beam steering systems according to certain embodiments of the invention adopt a design that uses a smaller number of discrete beam channels, for example 3-10, that are mechanically rotated with the gantry around the patient. The initial deflector at the exit of the accelerator rapidly steers beams into the channels as they rotate. Although the ideal is to eliminate the need for any mechanical moving parts, some advantages of this design include: arbitrary rotational angular resolution despite a fixed number of beam channels; reduced complexity and possibly cost given the smaller number of beam channels needed to achieve equivalent angular coverage; and the larger space between beam channels which makes it more straightforward to incorporate an x-ray source and detecting array for imaging, which when rotated provides integrated computed tomography imaging. The rate of mechanical rotation preferably provides full angular coverage sufficiently fast to freeze physiologic motion. The greater the number of beam channels, the less rotational speed required to meet this condition as a general matter.

One innovation of certain embodiments of the invention is to eliminate mechanical gantry rotation, thus a beam steering system with no mechanical moving parts. One such embodiment is illustrated in FIG. 1, in which there is a gantry through which a charged particle beam is electromagnetically steered or steered using radiofrequency deflection to the target from any axial direction and a limited range of non-coplanar directions in addition. An alternative implementation is to use multiple discrete beam ports arranged radially around the patient, with the beam being steered through each of the ports to the target for multidirectional beam arrangements. Another alternative implementation is to have multiple accelerating structures, one for each of a set of beam ports arranged radially around the patient.

Such novel treatment system geometries and steering systems can greatly enhance the treatment delivery speed of radiation therapy using any type of charged particle. Combining it with high-energy electrons in the 1-250 MeV range, more preferably the 50-250 MeV range, most preferably the 75-100 MeV range, has the following additional advantages: (1) Conformal dose distributions to both superficial and deep targets in patients superior to what can be achieved with conventional high-energy photon therapy; (2) Compactness of the source and power supply, which by using high-gradient accelerator designs such as those based wholly or partially on accelerators developed or in development at the SLAC National Accelerator Laboratory (SLAC) as described in Section C.iii below can accelerate electrons up to these energies in less than 2 meters; (3) Compactness of the gantry/beam ports compared to protons or ions because of the smaller electro-magnetic fields needed for electrons. This results in a system of comparable cost and physical size to existing conventional photon radiotherapy treatment systems, yet with better dose distributions and far faster dose delivery.

If treatment with photon beams is still desired, an alternative embodiment is to incorporate in this geometry an array of high density targets and collimator grid in place of a single target/multi-leaf collimator combination, one per beam port in the case of discrete beam ports, or mounted on a rapidly rotating closed ring and targeted by the scanned electron beam in the case of an annular beam port, in order to produce rapidly scanned, multidirectional photon beams. While this approach may be subject to the inefficiency of Bremsstrahlung conversion, the speed limitations of conventional mechanical gantry and multi-leaf collimator motions may be essentially eliminated. The main potential advantage of this implementation is that existing commercial electron linacs in a lower energy range could be used as the source.

In addition to extremely rapid dose delivery, certain embodiments of the invention naturally facilitate rapid image-guidance to ensure accuracy. By adjusting the energy of the scanned electron beam and directing it to an annular target or a fixed array of targets, with an appropriately arranged detector array, extremely fast x-ray computed tomography (CT) or digital tomosynthesis images can be obtained and compared to pre-treatment planning images immediately before delivery of the dose. Alternative embodiments can include integration of more conventional x-ray imaging or other imaging modalities, positron emission tomography and other options described in Section D.3 below.

C. Monte Carlo Simulation Design Considerations

One approach in designing certain embodiments of the invention is to proceed using some or all of the following: (1) Monte Carlo simulations to determine optimal operating parameters; (2) experimental measurements of VHEE beams to validate and calibrate the Monte Carlo codes; (3) implementation factors for practical, cost-efficient and compact designs for the systems; and (4) experimental characterization of key radiobiological aspects and effects.

1. Monte Carlo (MC) Simulation

MC simulations of VHEE of various energies have been performed on a sample case to estimate the range of electron energies needed to produce a plan comparable to optimized photon therapy. Dose distributions were calculated for a simulated lung tumor calculated on the CT data set of an anthropomorphic phantom.

Specifically, an optimized 6 MV photon beam Volumetric Modulated Arc Therapy Stereotactic Ablative Body Radiotherapy (VMAT SABR) plan calculated in the Eclipse treatment planning system; and simplistic conformal electron arc plans with 360 beams using a commonly available 20 MeV energy and a very high 100 MeV energy calculated with the EGSnrc MC code [Walters B, Kawrakow I, and Rogers D W O, DOSXVZnrc, Users Manual, 2011, Ionizing Radiation Standards National Research Council of Canada. p. 1-109. (http:irs.inms.nrc.ca/software/beamnrc/documentation/pirs794/), incorporated herein by this reference], were compared.

Figure 2A:
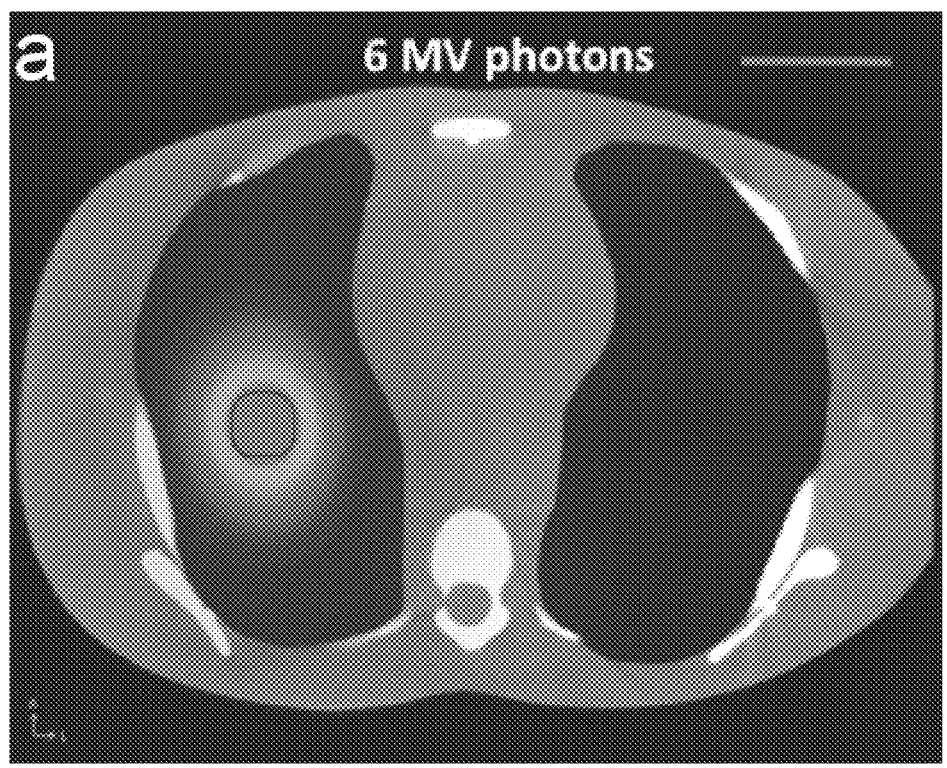
FIG. 2 shows comparative simulation results of SABR for an early stage lung tumor using 6 MV photons, 20 MeV electrons, and 100 MeV electrons.
Figure 2B:
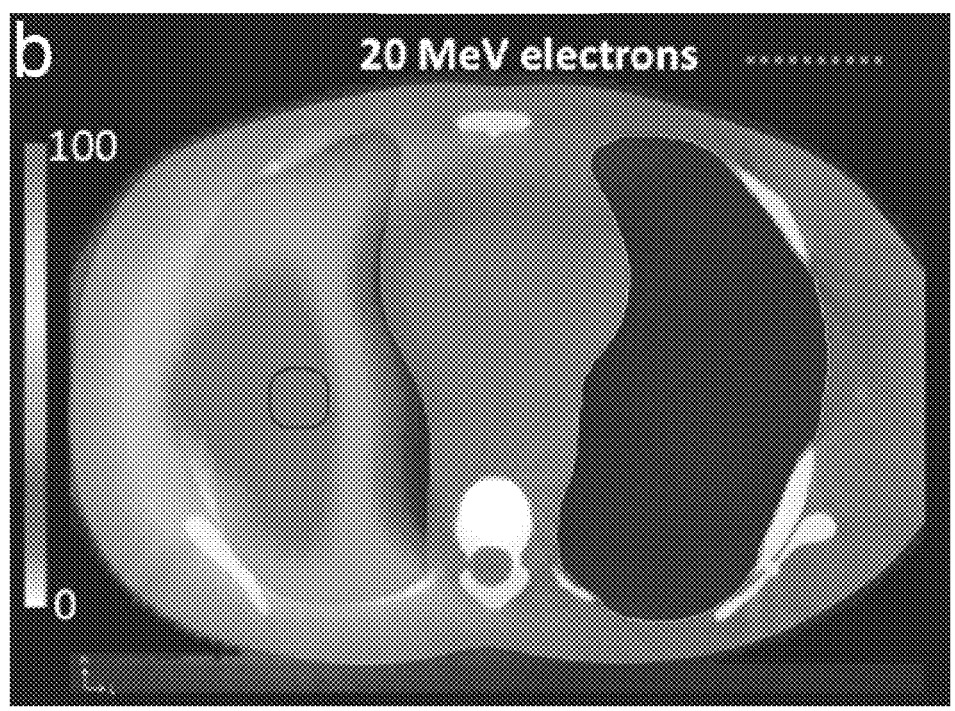

FIG. 2 shows axial images of simulation of SABR for an early stage lung tumor: dose distribution in an anthropomorphic phantom for a state-of-the-art 6 MV photon VMAT plan (FIG. 2a), a conformal electron arc plan using currently available 20 MeV electron beam (FIG. 2b), and a conformal electron arc plan using a 100 MeV electron beam as might be delivered by an embodiment of the invention (FIG. 2c). A graphical representation shows dose volume histogram ("DVH") of the planning target volume ("PTV") (delineated in black in the axial images) and critical organs: DVHs for 6 MV photons are shown in solid, 20 MeV electrons in dotted, and 100 MeV electrons in crossed lines (FIG. 2d). The plans were normalized to produce the same volumetric coverage of the PTV by the prescription dose. While conventional 20 MeV electrons results in poor conformity, the 100 MeV electron plan, even without optimization, is slightly more conformal than the 6 MV photon VMAT plan. Simulating conformal electron arcs across an energy range of 50-250 MeV (FIGS. 2e, 2f) demonstrates that both the high (100%) and intermediate (50%) dose conformity indices (CI100% and CI50%) as well as the mean lung dose and total body integral dose are superior for electron energies of ~80 MeV and higher for this selected clinical scenario. With inverse optimization, superior plans with even lower electron energies should be possible.

As shown in FIG. 2, the axial views of the dose distributions demonstrate that when all the plans are normalized to produce the same volumetric coverage of the target, the dose conformity of the 20 MeV beam is poor whereas the 100 MeV electron beam, even without inverse optimization, generates a dose distribution equivalent to the state-of-the-art 6 MV photon beam VMAT plan. In fact, the DVH's of the target and critical structures for the three beams demonstrate slightly better sparing of critical structures with the 100 MeV electron plan compared to the 6 MV photon plan. As shown in FIGS. 2e and 2f at electron energies above ~80 MeV, simple conformal electron arc plans (normalized to produce the same volumetric coverage of the target) are superior to the optimized 6 MV photon VMAT plan in terms of conformity, with conformity index defined as the ratio of the given percent isodose volume to the PTV, and the normal organ doses (mean lung dose and total body integral dose (expressed in arbitrary units normalized to the photon plan). In preliminary simulations of this selected clinical scenario, the inventors have found electron energies of 75-100 MeV to produce plans of comparably high to superior quality compared to the best photon plans, and anticipate that plan optimization will produce superior plans with even lower electron energies. For example, the inventors have used Monte Carlo simulations to demonstrate that an 8 cc lung tumor could be treated with 100 MeV electrons to a dose of 10 Gy in 1.3 seconds.

Further optimization of the electron plan can help to define the minimum electron beam energy with a comparable dose distribution to the best photon VMAT plan. In preliminary simulations of this selected clinical scenario, the inventors have found electron energies of 75-100 MeV to produce plans of comparably high quality to the best photon plans, and anticipate superior plans with plan optimization.

2. Experimental Measurement of VHEE Beams a. Monte Carlo Simulations

Figure 3:
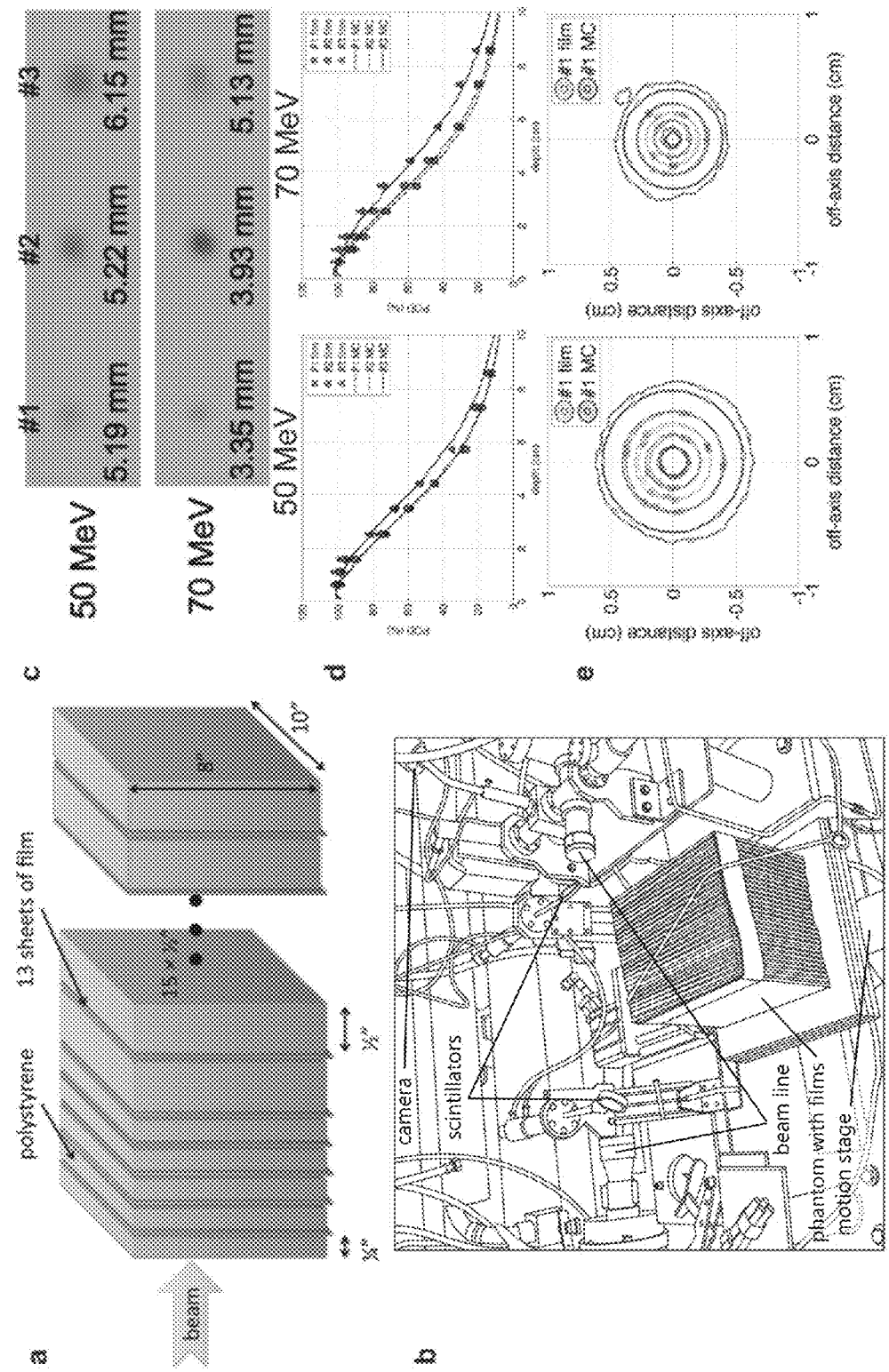
FIG. 3 is a schematic (a) and photograph (b) of the experimental setup for film measurements (c) of very high energy electron beams at the Next Linear Collider Test Accelerator (NLCTA) beam line at the SLAC National Accelerator Laboratory (SLAC), together with Monte Carlo simulations (solid lines) and film measurements (markers) of percentage depth dose curves (d) and beam profiles taken at 6 mm depth (e) for 50 MeV and 70 MeV beams, respectively.

To demonstrate the accuracy of Monte Carlo calculations with VHEE beams, the inventors experimentally measured the dose distribution and depth dose profiles at the NLCTA facility at SLAC. Of note, the NLCTA employs compact high-gradient linear accelerator structures which can produce beams that are relevant to those potentially suitable for certain embodiments of the invention. The inventors assembled a dosimetry phantom by sandwiching GAFCHROMIC EBT2 films (international Specialty Products, Wayne, N.J.) between slabs of tissue equivalent polystyrene as shown in FIG. 3. FIG. 3a is a schematic and FIG. 3b is a photograph of the experimental setup for film measurements (FIG. 3c) of very high-energy electron beams at the NLCTA beam line SLAC. Monte Carlo simulations and film measurements of percentage depth dose curves (FIG. 3d) and 2-D dose distributions taken at 6 mm depth (FIG. 3e) for 50 MeV and 70 MeV beams demonstrate a high degree of agreement between calculation and measurement.

By way of procedure and in greater detail, the phantom as shown in FIG. 3a was irradiated with 50 MeV and 70 MeV beams. Three beam sizes ranging from 3.35 to 6.15 mm were tested for each energy level. The energy was measured by a spectrometer upstream from the location of the experiment and the beam size was measured by two scintillating screens using two cameras just before and after the phantom with the phantom removed from the beam line (FIG. 3b). The films were calibrated with a clinical electron beam at 12 MeV. MC simulations have demonstrated no energy dependence of the film response at electron energies above 1 MeV. The number of particles required to irradiate the films to dose levels between 1-5 Gy to match the dynamic range of the film was determined for each beam size using MC simulations and used in the experiment. The charge was set to 30 pC/pulse corresponding to $1.9 \times 10^8$ electrons and the pulse rate was reduced to 1 Hz for easier control of the exposure. The number of pulses varied from 2 to 40 pulses depending on the beam size. The experimental and calibration films were read out in a flatbed scanner (Epson Perfection V500, Long Beach, Calif.) with 0.1 mm pixels 24 hours after irradiation (FIG. 3c) and central axis percentage depth dose (PDD) curves and 2-dimensional dose distributions at various depths were plotted. The experimental setup was simulated in the MCNPX 5.0 MC code [Palowitz DB, MCNPX User's Manual, Version 2.7.0, 2011 (http://mcnpx.lanl.gov/documents.html) incorporated herein by this reference].

The simulations are compared to measurements in FIG. 3d-e. Good agreement was observed for both the PDD curves and beam profiles for 50 and 70 MeV. These preliminary results indicate that dose from VHEE beams can be measured with GAFCHROMIC films and that VHEE beams can be accurately simulated with the GEANT4 code.

In the arrangement shown in FIG. 3b, a 50-µm vacuum window made of stainless steel was used to interface the accelerator line with open air, in which the dose phantom (FIG. 2a) was placed. The stainless window was found to cause significant angular beam spreading, so that the simulations were also performed with a beryllium window which imparted less beam spreading. While a vacuum window is necessary to separate the vacuum of the accelerator beam line from the open air and the patient, significant angular spread will adversely affect beam performance and clinical accuracy. The angular spread from a thinner beryllium window was still present but it was much smaller than steel, due to beryllium's low atomic number.

b. Cross Validation of Monte Carlo Codes

Figure 4:
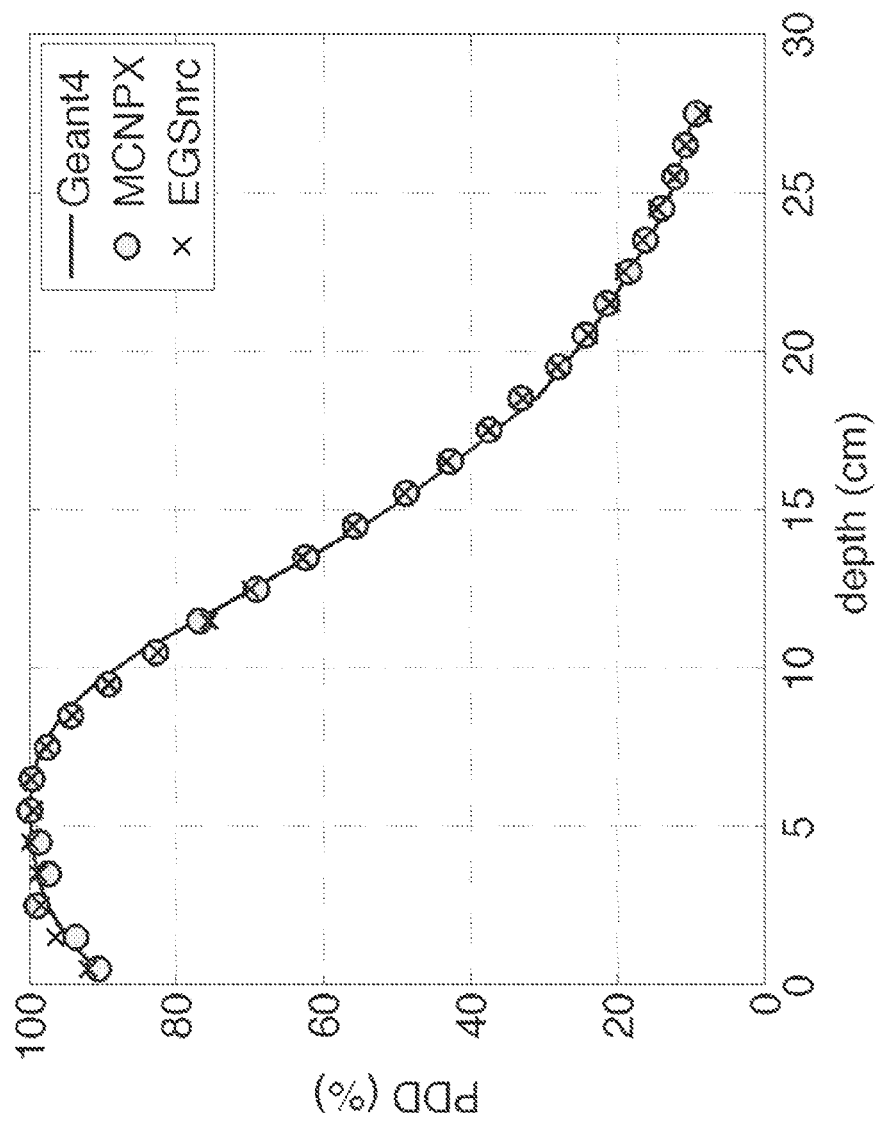
FIG. 4 shows graphic representations of percentage depth doses for a 2×2 cm 100 MeV electron beam in a water phantom, simulated using three independent Monte Carlo codes.
Figure 7:
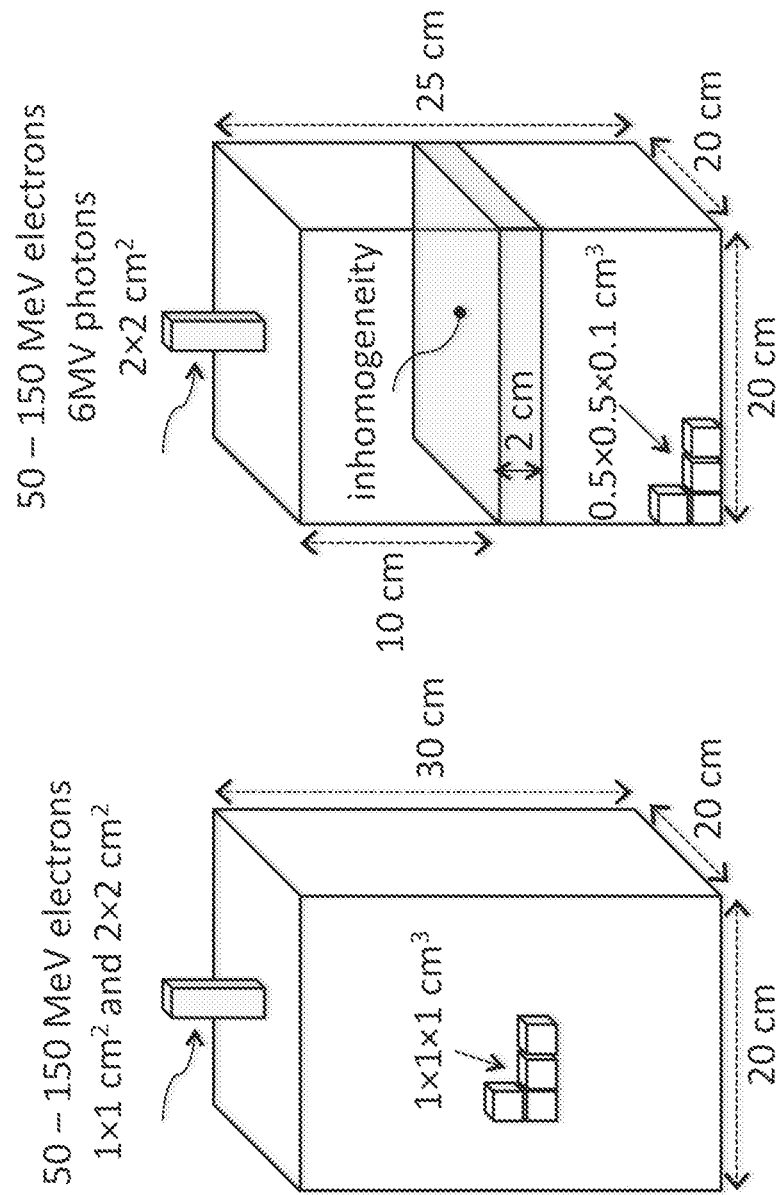
FIG. 7 shows water phantoms used in Monte Carlo simulations conducted in accordance with certain embodiments of the invention.

The inventors performed Monte Carlo simulations using three independent codes for identical geometries to determine the consistency of calculated doses. The dose deposition of a number of rectangular electron beams incident on a 20×20×30 cm water phantom (as shown in FIG. 7a) was simulated in the GEANT4, MCNPX, and EGSnrc MC codes. The simulated electron beam energies were 50, 75, 100, and 150 MeV with beam sizes of 1×1 cm and 2×2 cm. The central-axis PDDs were plotted and compared for all three MC codes. Excellent agreement was found between the codes for all of these comparisons, as shown in FIG. 4, which shows PDD for a 2×2 cm 100 MeV electron beam, simulated using the three Monte Carlo codes.

c. VHEE Tissue Interactions

Figure 5:
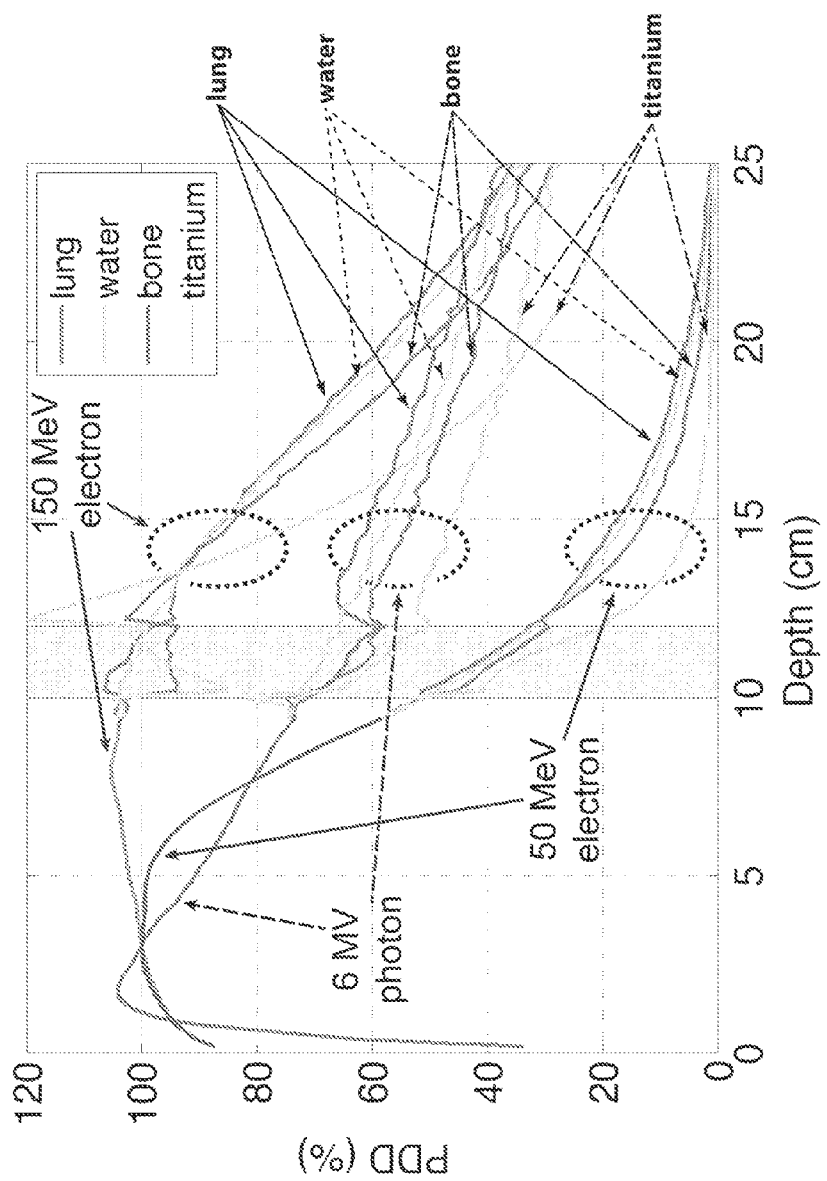
FIG. 5 shows graphic representations of percentage depth doses for 2×2 cm 50 and 150 MeV electron beams compared to 6 MV photons in a water phantom, with 2 cm thick heterogeneous tissue at 10 cm depth.

Monte Carlo simulations were performed to evaluate the impact of various tissue heterogeneities on VHEE beams relative to MV photon beams. FIG. 5 shows PDD curves for 2×2 cm 50 and 150 MeV electron beams compared to 6 MV photons in a water phantom with 2 cm thick heterogeneous tissue at 10 cm depth, normalized to identical dose at 3 cm depth. As shown in FIG. 5, the 50 and 150 MeV VHEE beams are less sensitive to tissue heterogeneity over the density range from lung tissue to titanium prosthetic implants compared to 6 MV photons.

Figure 6:
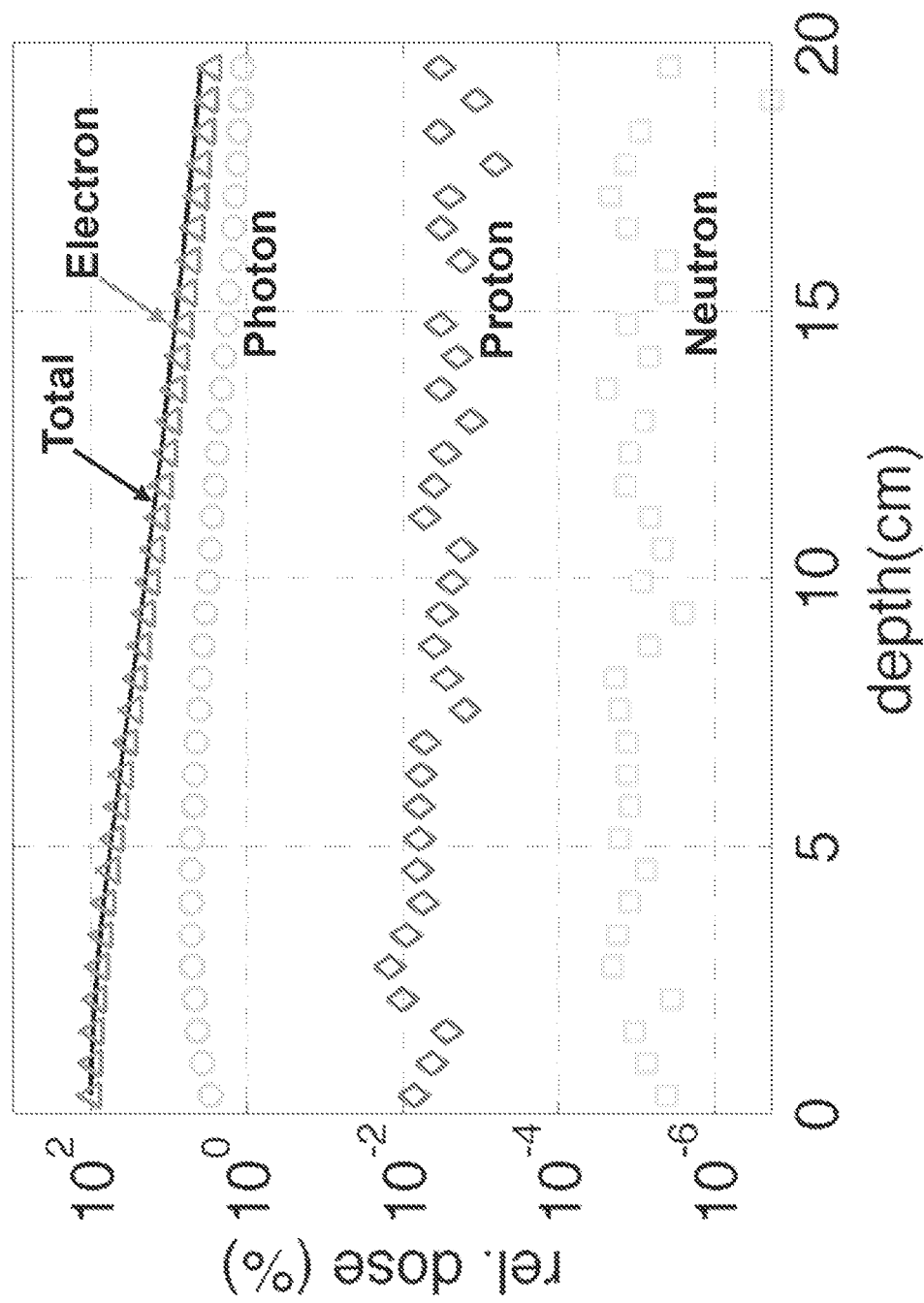
FIG. 6 shows graphic representations of relative contribution to dose from a 100 MeV electron beam vs. secondary generated particles (logarithmic scale).

Contribution of secondary particles produced by Bremsstrahlung and electronuclear interactions to the dose from VHEE beams were also analyzed. FIG. 6 shows relative contribution to dose from a 100 MeV electron beam vs. secondary generated particles (log scale). As shown in FIG. 6, for a 100 MeV electron beam, nearly all the deposited dose is due to electrons, with a minor contribution from Bremsstrahlung x-rays, and far lower dose from protons and neutrons. FIG. 6 also shows that dose from neutrons is far less than with 15-18 MV photons or high-energy protons. This holds for 50 and 70 MeV electrons as well (not shown). For a 25 Gy SABR treatment of a 2 cm diameter target, an upper limit of total body neutron dose is estimated to be 0.6 mSv based on MC simulations. This is in contrast to more than 1-2 orders of magnitude greater estimated neutron doses of 9-170 mSv for scanning beam proton therapy and 15-18 MV photon IMRT for the same clinical scenario, based on published measurements of ambient neutron doses [Schneider U, Agosteo S, Pedroni E, and Besserer J., "*Secondary neutron dose during proton therapy using spot scanning*," International Journal of Radiation Oncology Biology Physics, 2002; 53(1): 244-251. (PMID): 12007965); Howell R M, Ferenci M S, Hertel N E, Fullerton G D, Fox T, and Davis L W, "*Measurements of secondary neutron dose from* 15 *MV and* 18 *MV IMRT*," Radiation Protection Dosimetry, 2005; 115(1-4): 508-512. (PMID: 16381776) both of which are incorporated herein by this reference]. An advantage of such potential designs according to certain embodiments compared to >8 MV photon and scanning beam or passive scattering proton therapies is elimination of need for beam modifying structures prior to beam incidence on the patient, in which most neutrons are generated with existing modalities.

d. Tissue Inhomogeneities

The effect of tissue inhomogeneities on dose deposition of VHEE beams has been studied by the inventors, A 20×20×25 cm3 water phantom with 0.5×0.5×0.1 cm3 voxels and a 2-cm thick inhomogeneity placed at 10 cm depth was built (FIG. 7b). The 2-cm thick slab was consequently filled with lung with mass density ρ of 0.368 g/cm3, adipose (ρ=0.950 g/cm3), ribs (ρ=1.410 g/cm3), and cortical bone (ρ=1.920 g/cm3) tissue to assess the effect of human tissue inhomogeneities. The tissue composition was obtained from the ICRU-44 document [ICRU. Tissue substitutes in radiation dosimetry and measurement, 1989 (incorporated herein by this reference)]. Moreover, the effect of metals, such as hip prostheses, dental fillings, and surgical clips, was investigated by simulating a steel slab (ρ=8.030 g/cm3). Doses deposited by 50, 100, and 150 MeV electron beams, as well as 6 MV photon beam interacting with the inhomegeneity slab were simulated. The DOSXYZnrc code was chosen for this task due to its simplicity of use and its shortest calculation times. The statistical uncertainties in all central axis voxels were below 1%.

3. Ultra-High Gradient Accelerator Structure Design

Pluridirectional very high electron energy radiation therapy systems and processes according to various embodiments of the invention can be created with various types of electron source. There are a number of potential sources of very high-energy electrons in the range of, for example, up to about 250 MeV. A non-exhaustive list includes cyclotrons, synchrotrons, linacs (which can include more conventional designs with greater length), racetrack microtrons, dielectric wall accelerators, and laser plasma wakefield accelerator sources. Some of these are large and would need to be housed in a separate room. Some are not very mature technologies. In terms of goals of certain embodiments of the invention which can include any or all of compactness (entire system fitting within existing medical linac vaults without a separate room), power requirements, cost, repetition rates, compatibility with intensity modulation techniques described in this document, and other practical considerations, compact very high-gradient standing wave linear accelerators such as those developed at SLAC as described in the two paragraphs immediately below, or derivatives of them, may be at least a logical starting point, although other currently existing or future options should not be ruled out.

Highly efficient π-mode standing wave accelerator structures have been developed at SLAC for the project formerly known as the Next Linear Collider, a positron-electron collider at 500 GeV energy for high-energy physics research [Dolgashev V, Tantawi S, Higashi Y, and Spataro B, "*Geometric dependence of radio-frequency breakdown in normal conducting accelerating structures*," Applied Physics Letters, 2010; 97(17). (http://apl.aip.org/resource/1/applab/v97/i17/p171501_s1) incorporated herein by this reference (hereinafter sometimes "Dolgashev 2010"]. Such accelerators are capable of accelerating electrons to 100 MeV within 1 meter [Id.] using an optimized accelerating waveguide powered by a 50 MW 11.4 GHz microwave generator (klystron) [Caryotakis G. Development of X-band klystron technology at SLAC. Proceedings of the 1997 Particle Accelerator Conference, 1997; 3: 2894-2898. (http://ieeexplore.ieee.org/xpls/abs_all.jsp?arnumber=752852) incorporated herein by this reference]. In order to produce a practical system in terms of cost and size, optimized designs according to certain embodiments of the invention allow both economical production and high performance to minimize the treatment time while allowing maximum possible flexibility in beamlet shapes, directionality, and energy.

Furthermore, it has been shown that coupling a series of small sections of standing-wave accelerators with a distributed radiofrequency (RF) network makes it possible to design a system without any reflection to the RF source [Tantawi S G, "*rf distribution system for a set of standing-wave accelerator structures*," Physical Review Special Topics-Accelerators and Beams, 2006; 9(11) (http://prstab.aps.org/abstract/PRSTAB/v9/i11/e112001) incorporated herein by this reference (hereinafter, "Tantawi 2006"]. Building on these developments, a practical implementation of a standing-wave accelerator structure has been designed [Neilson J, Tantawi S, and Dolgashev V, "Design of RF feed system and cavities for standing-wave accelerator structure," Nuclear Instruments and Methods in Physics Research A: Accelerators, Spectrometers, Detectors and Associated Equipment, 2011; 657(1): 52-54. (http://www.sciencedirect.com/science/article/pii/S0168900211008898) incorporated herein by this reference (hereinafter, "Neilson 2011"] that is designed to accelerate electrons to 100 MeV within one meter. Such accelerators can serve as a basis for or be relevant to certain embodiments of the invention.

D. Other Design Issues

1. Design Options for the Injector System

To inject the required low charge bunch into accelerators according to certain embodiments of the invention, several possibilities are available. Those include a photo-injector RF gun. Additional options can be considered to reduce the cost and size of the system, including a variety of field emitter configurations and RE thermionic guns.

2. Optimization of the RF Source by the Addition of a Pulse Compression System

RF source requirements depend ultimately, at least in part, on the accelerator design. With the optimized cavities as described above, it is projected that a 50 MW source at X-band will be sufficient for a 2 meter accelerator operating at 50 MV/m. This type of source is available at SLAC and is being commercialized by Communications & Power Industries (Palo Alto, Calif.). With the use of a pulse compression system it may be possible to either reduce the cost and sophistication of the RF source dramatically or make the accelerator structure more compact by reducing the length to 1 meter. Because the typical filling time of such a structure is about 100 ns and the RF source typically provides several μs long pulses, one can use a compact pulse compressor with a high compression ratio and a power gain of about 3.5 to reduce the required RF source power to only about 14 MW, which opens the door for a variety of sources, including sources that are commercially available now, and including those that include a pulse compression system.

3. Imaging and Target Position Verification Options

Given that treatment according to certain embodiments of the invention is delivered sufficiently fast to freeze physiologic motion, it is important to verify that the target is in the planned position at the time the treatment is triggered or administered. Several dynamic or "real-time" imaging or other localization technologies can be integrated into certain embodiments of the invention for this purpose. Potential such implementations can include any of the following, alone or in combination:

a. Integration of two or more x-ray fluoroscopic imaging devices, forming at least one orthogonal pair, to permit real-time 3-dimensional verification of alignment of bony anatomy and/or implanted radio-opaque fiducial markers.

b. Dynamic optical surface scanning, ideally combined with an internal imaging modality such as CT or fluoroscopy, providing real-time correlation of the external surface to the internal target position.

c. Integration of fast x-ray computed tomography. This can be accomplished by the addition of a relatively conventional multi-detector CT system within the gantry of the treatment system. Alternatively, if a continuous ring gantry design is used for the treatment delivery system, the treatment system itself can be used to scan a low energy (around 100 keV) electron beam across a ring-shaped target introduced into the beam path to produce a rapidly moving x-ray source for very fast CT scanning, known as "electron beam CT" immediately before switching to the high energy treatment beam.

d. Implantable radiofrequency beacons, whose 3-dimensional position can be read out in real time by an external antenna array. Beacons can be implanted in or near the target and serve as surrogates for the target position.

e. Integration of ultrasound. For certain anatomic locations, for example the upper abdomen and pelvis, ultrasound can provide continuous real-time 3-dimensional localization of targets.

f. While the most technologically complex to implement, magnetic resonance imaging may be implemented, which can provide real-time 3-dimensional localization of targets. Integration of MRI with conventional photon therapy systems is already commercially available or under development by multiple vendors.

In any of these implementations, dynamic visualization and/or automated image analysis tools can be used to permit either manual triggering of the treatment by the operator, or automated triggering with manual override.

4. Implementation of Intensity Modulation

According to certain embodiments of the invention, which may be used with various types of accelerators in accordance with the invention, and in order to achieve highly conformal volumetric dose shaping, radiation fields from each of multiple beam directions can cover an area with varying beam intensity across the field, with the intensity patterns optimized to produce the desired 3-dimensional dose distribution when summed across all beam directions. Such intensity modulation may be produced by raster scanning individual beamlets of varying intensity across the field from each beam direction. Alternatively, it may be produced by using a 2-dimensional intensity-modulated electron pattern at the source, effectively an array of beamlets of varying intensity, and accelerate and steer the entire array to the target volume. This eliminates the need for a raster scanning mechanism at the exit of each of the beam channels, greatly simplifying the design and reducing the bulk and cost of those components, and increases the treatment delivery speed by delivering beamlets in parallel within a much smaller number of electron pulses or bunches.

According to some embodiments, the intensity modulation of the electron source may be produced by using a photocathode illuminated by a light source with the corresponding intensity pattern, in effect, an optical image. One implementation is to use a laser as the light source, and a digital light processing (DLP) micromirror array or other intensity modulating device to produce the charge image on the photocathode to be accelerated and steered. The electron beam optics can be designed to maintain the pattern with high fidelity until it reaches the target.

Figure 8:
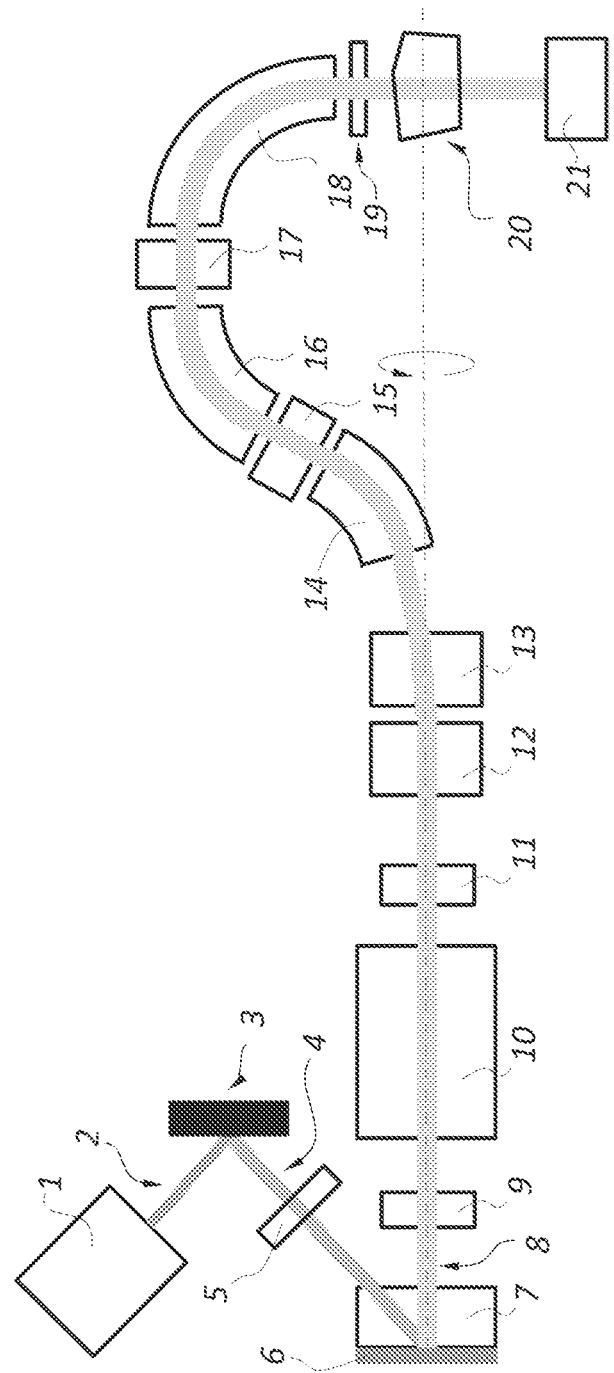
FIG. 8 schematically shows portions of a radiation treatment system with modulation of electron beam transverse profile using pulse-to-pulse modulation of injection laser beam profile impacting a photocathode of an electron injector.

According to one nonlimiting embodiment as shown in FIG. 8, a short, typically picosecond-long pulse with uniform transverse profile is generated by a laser (1). The wavelength of the laser is matched with specific photocathode material to obtain required charge and emittance. The laser pulse (2) falls on a digital-micro-mirror device (3), Pixels of this micromirror device are controlled by a computer and will reflect a portion of the laser pulse (4) thus creating an image that is then transferred to the photocathode (6) using precision projection optics (5). Although various types of accelerators may be used with this embodiment, high gradient pulsed devices with a few milliseconds between pulses are preferable. The computer modulates the mirror array thus creating a new image for each consequent pulse. A laser pulse with amplitude-modulated transverse profile that impacts the photocathode (6) will create an electron replica of the laser pulse transverse profile (8). The photocathode (6) is a part of photoelectron gun (7). The gun creates an electric field on the photocathode which accelerates the transverse-modulated electron beam. The gun also provides initial focusing for the electron beam. The electron beam then passes through the low-aberration focusing system toward accelerator (10). The accelerator increases energy of the beam to a desired value. The electron beam then passes through focusing optics (11) toward horizontal (12) and vertical (13) fast deflectors. The deflectors are controlled by a computer and are able to send the electron beam in different directions for each consecutive accelerator pulse. The desired direction will depend on (among other things) specific realization of the gantry's beam lines, number of the beam lines and whether they are movable or not. For clarity only one gantry beam line is shown in FIG. 8. After the deflectors, the electron beam passes through bending magnets (14, 16, 18) and electron optics (15, 17) and is directed through electron-beam monitoring system (19) toward the target (20). The transversely modulated electron beam irradiates the target with required distribution of the dose. After passing through the target, the beam is sent toward beam dump (21) in order to reduce unwanted radiation exposure of the target.

Of note, a greater degree of intensity modulation will produce more conformal dose distributions. However, with conventional photon therapy where intensity modulation is delivered in a serial fashion over time, more modulation comes at a cost of longer delivery time, more leakage dose to the patient, and greater uncertainty in delivered dose because of target and organ motion during the longer treatment delivery time and its interplay. With VHEE technology according to certain embodiments of the invention, all of these problems are circumvented: arbitrarily complex intensity modulation can be produced through optical imaging, and rapid parallel delivery eliminates uncertainty from interplay effects.

The concept of conversion of an optical intensity pattern into a radiation intensity pattern within a patient is considered to be unique, and also uniquely applicable to electron beam therapy in accordance with embodiments of the invention as opposed, for example, to photon or proton or other particle therapies.

E. General

Numerous specific details are set forth herein to provide a thorough understanding of the claimed subject matter. However, those skilled in the art will understand that the claimed subject matter may be practiced without these specific details. In other instances, methods, apparatuses or systems that would be known by one of ordinary skill have not been described in detail so as not to obscure subject matter that may be claimed.

While the present subject matter has been described in detail with respect to specific embodiments thereof, it will be appreciated that those skilled in the art, upon attaining an understanding of the foregoing may readily produce alterations to, variations of, and equivalents to such embodiments. Accordingly, it should be understood that the present disclosure has been presented for purposes of example rather than limitation, and does not preclude inclusion of such modifications, variations and/or additions to the present subject matter as would be readily apparent to one of ordinary skill in the art.

What is claimed is:

1. A system for delivering a particle beam to a targeted tissue in a patient, comprising:
   one or more accelerators, each of the one or more accelerators configured to generate one or more particle beams;
   one or more beam steering devices configured for receiving the one or more particle beams from the one or more accelerators and steering the one or more beams to the target tissue from multiple directions; and
   a controller configured for controlling a length of time that the particle beam irradiates the targeted tissue in delivering an entire treatment dose, the length of time of delivering the entire dose being less than 10 seconds.

2. The system of claim 1, the system further comprising:
   a plurality of discrete beam ports arranged about the patient, wherein the one or more beam steering devices are configured to steer multiple beams from the one or more accelerators through the multiple discrete beam ports without requiring movement of mechanically moving parts.

3. The system of claim 2, wherein the one or more accelerators comprise a single accelerator and the one or more beam steering devices are configured to steer multiple beams from the single accelerator to the targeted tissue from multiple directions through the multiple discrete beam ports.

4. The system of claim 1, the system further comprising:
at least one beam port through which multiple beams are directed to the targeted tissue, wherein the at least one beam port is movable relative to the targeted tissue to provide additional angles for delivery of the multiple beams to the targeted tissue from multiple directions.

5. The system of claim 1, the system further comprising:
wherein the at least one beam port is supported by a gantry configured to extend at least partly about the patient, the gantry being movable and/or rotatable relative to the targeted tissue.

6. The system of claim 1, the system further comprising:
a continuous beam port configured such that the one or more beams are directed through the continuous beam port whereby the one or more beams can be directed to the targeted tissue from a range of angles.

7. The system of claim 1, the system further comprising:
an annular ring-like beam port through which the one or more beams are directed to the targeted tissue from multiple directions.

8. The system of claim 1, wherein the one or more accelerators comprises multiple accelerators, one for each port of a plurality of beam ports arranged about the patient, wherein the one or more beam steering devices are configured such that steering multiple beams from the multiple accelerators through the respective beam ports directs the multiple beams to the targeted tissue from multiple directions without requiring movement of mechanically moving parts.

9. The system of claim 8, wherein the plurality of beam ports are movable relative to the targeted tissue such that moving the plurality of beam ports provides additional angles for delivery of the multiple beams to the targeted tissue.

10. The system of claim 9, wherein the plurality of beam ports are supported by a gantry configured to extend at least partly about the patient, wherein the gantry is movable and/or rotatable relative to the targeted tissue such that movement and/or rotation of the gantry moves the plurality of beam ports sufficiently to provide the additional angles for delivery.

11. The system of claim 1, wherein the system is configured such that the one or more particle beams comprises any of an electron beam and a photon beam.

12. The system of claim 1, wherein the particle beam of the one or more accelerators comprises a very high electron energy beam comprising an electron energy beam between 1 and 250 MeV.

13. The system of claim 11, further comprising:
a plurality of beam ports through which the one or more electron beams are directed; and
one or more photon sources positioned at one or more beam ports of the plurality of beam ports such that delivering the electron beam through the one or more beam ports creates a photon beam.

14. The system of claim 12, wherein at least some of the one or more photon sources are in a fixed position.

15. The system of claim 11, further comprising:
a plurality of beam ports through which the one or more electron beams are selectively directed; and
at least one photon source selectively positionable at one or more beam ports of the plurality such that directing the one or more electron beams through one or more beam ports at which the at least one photon source is positioned creates a photon beam, wherein the system is configured to provide multiple photon beams from multiple directions by moving the at least one photon source between multiple beam ports through which the one or more electron beams are directed.

16. The system of claim 11, wherein the plurality of beam ports are disposed on a beam port support structure configured to extend at least partly about the patient and the at least one photon source is disposed on a photon source support structure movable and/or rotatable relative to the beam port support structure.

17. The system of claim 13, wherein the photon source comprises any of a single target, a target array, a collimator grid and a multi-leaf collimator.

18. The system of claim 1, further comprising:
one or more deflectors that deflect the one or more beams received from the one or more accelerators through one or more channels to one or more exit ports before delivery to the targeted tissue, wherein each of the one or more beams exit the respective exit port at an associated exit angle and an associated beam size.

19. The system of claim 18, wherein the one or more beams comprise multiple beams deflected through multiple channels that are directed to the targeted tissue from the exit channels of the multiple channels from multiple directions within a range of non-coplanar directions.

20. The system of claim 18, wherein the system is configured such that the exit angle is perpendicular to a longitudinal axis of the patient.

21. The system of claim 18, wherein the system is configured to change the exit angle and/or to change a beam size of the one or more beams exiting the beam ports to adapt to a particular treatment plan.

22. The system of claim 1, further comprising:
an imaging or targeting system configured to provide rapid imaging and/or rapid targeting for delivery of the particle beam to the targeted tissue within the length of time.

23. The system of claim 22, wherein the imaging or targeting system is configured to obtain an image of the targeted tissue and/or targeted location of the targeted tissue immediately before delivery of the particle beam.

24. The system of claim 23, wherein the controller is configured to control delivery of the particle beam to the targeted tissue based on a comparison between the image and a pre-treatment planning image.

25. The system of claim 1, wherein the controller is configured such that the length of time of delivering the entire dose is less than one second.

26. The system of claim 1, wherein the one or more beam steering devices are selected from the group consisting of electro-magnetic devices and radiofrequency deflector devices.

27. The system of claim 1, wherein the one or more beam steering devices are capable of providing thin pencil beam raster scanning.

28. The system of claim 1, wherein the one or more beam steering device are capable of providing volume filling scanning.

29. A method for treating a patient, said method comprising:
providing a system for delivering a treatment dose of radiation to a targeted tissue in the patient;
generating one or more particle beams and accelerating the one or more particle beams with one or more accelerators of the system;
steering the one or more beams received from the one or more accelerators to the targeted tissue from multiple directions with one or more beam steering devices of the system; and
irradiating the targeted tissue with the one or more beams directed to the targeted tissue for a controlled length of time, the length of time being less than 10 seconds.

30. The method of claim 29, wherein generating one or more particle beams comprises generating multiple particle beams with the one or more accelerators and steering the multiple particle beams through multiple discrete beam ports arranged about the patient without requiring movement of mechanically moving parts.

31. The method of claim 29, wherein generating one or more particle beams comprises generating multiple particle beams with one more accelerators and steering the multiple particle beams through at least one beam port to the targeted tissue; and
moving the at least one beam port to provide additional angles from which the multiple particles beams are directed to the patient.

32. The method of claim 29, wherein generating one or more particle beams comprises generating multiple particle beams with one more accelerators and steering the multiple particle beams to the targeted tissue through at least one beam port on a gantry extending at least partly about the patient; and
moving and/or rotating the gantry to provide additional angles from which the multiple particles beams are directed to the targeted tissue through the at least one beam port.

33. The method of claim 30, wherein generating one or more particles beams with one or more accelerators comprises generating one or more particle beams with a single accelerator.

34. The method of claim 29, wherein steering the one or more beams comprises steering multiple beams through a continuous beam port to the targeted tissue from multiple directions within a range of angles.

35. The method of claim 29, wherein steering the one or more beams comprises steering the one or more beams from multiple directions through an annular ring-like beam port on a gantry that extends at least partly around the patient.

36. The method of claim 29, wherein steering the one or more beams comprises steering one or more beams from each of multiple accelerators through a plurality of beam ports, each accelerator corresponding to a beam port of the plurality of beam ports.

37. The method of claim 36, wherein the multiple beams are steered to the targeted tissue from multiple directions through the plurality of beam ports without movement of any mechanically moving parts.

38. The method of claim 36, further comprising:
moving the plurality of beam ports relative to patient to provide additional angles from which the multiple particles beams are directed to the targeted tissue through the plurality of beam ports.

39. The method of claim 36, wherein steering the one or more beams through a plurality of beam ports comprises steering the one or more beams through the plurality of beam ports, which are provided on a gantry extending at least partly about the patient, the method further comprising:
moving and/or rotating the gantry to provide additional angles from which the multiple particles beams are directed to the targeted tissue through the plurality of beam ports.

40. The method of claim 29, further comprising:
deflecting the one or more beams received from the one or more accelerators through one or more channels of the system to exit through one or more corresponding exit ports of the one or more channels, wherein each of the one or more beams exit the respective exit port at an associated exit angle and an associated beam size.

41. The method of claim 40, wherein deflecting the one or more beams comprises deflecting multiple beams through multiple channels to the targeted tissue from the exit channels of the multiple channels from multiple directions within a range of non-coplanar directions.

42. The method of claim 40, wherein deflecting the one or more beams through the one or more channels comprises deflecting the one or more beams through the one or more channels to exit the respective exit port at the associated exit angle such that the one or more beams are perpendicular relative to a longitudinal axis of the patient.

43. The method of claim 40, further comprising:
changing the exit angle and/or the beam size of the one or more beams exiting the exit ports to adapt to a particular treatment plan.

44. The method of claim 29, wherein generating one or more particle beams comprises generating one or more electron or photon energy beams.

45. The method of claim 44, wherein generating one or more particle beams comprises generating one or more beams comprise one or more electron energy beams between 25 and 100 MeV.

46. The method of claim 44, further comprising:
steering the one or more electron energy beams through a photon source before delivery to the targeted tissue.

47. The method of claim 29, further comprising:
obtaining an image of the targeted tissue immediately before delivering the one or more particle beams to the targeted tissue for irradiation treatment; and
controlling delivery of the one or more particle beams to the targeted tissue with a controller of the system based on the image of the targeted tissue.

48. The method of claim 47, further comprising:
obtaining one or more pre-treatment planning images of the targeted tissue;
planning a treatment using the one or more pre-treatment planning images; and
controlling delivery of the particle beams to the targeted tissue based on a comparison between the image and the one or more pre-treatment images.

49. The method of claim 29, further comprising:
obtaining imaging or targeting location information of the targeted tissue with an imaging or targeting device and determining a position of the targeted tissue based on the imaging or targeting location information; and
controlling directional delivery of the one or more beams to the targeted tissue using one or more beam steering devices based on the determined position and completing delivery of the entire dose before substantial movement of the targeted tissue from the determined position of the targeted tissue.

50. The method of claim 29, wherein irradiating the tissue comprises delivering multiple beams to the targeted tissue from multiple predetermined directions concurrently or in rapid succession at multiple predetermined points in time completing delivery of the entire dose from the multiple predetermined directions within less than 10 seconds.

51. A method for treating a patient, comprising:
generating one or more particle beams of varying beam intensity, wherein each of the one or more particle beams covers an area of the targeted tissue with varying beam intensity according to a treatment pattern of desired radiation dose distribution;
accelerating the one or more particle beams of varying beam intensity with one or more accelerators; and
steering the one or more particle beams of varying beam intensity to the targeted tissue with one or more beam steering devices from one or more directions.

52. The method of claim 51, wherein the one or more particle beams of varying beam intensity comprise an array of beamlets of varying intensity.

53. The method of claim 52, wherein the array of beamlets of varying intensity is produced by raster scanning individual beamlets of varying intensity from each beam direction of the one or more directions or by using a two-dimensional intensity-modulated electron pattern.

54. The method of claim 53, further comprising:
projecting or scanning the two-dimensional intensity-modulated electron pattern on a photocathode.

55. A system for treating a patient, comprising:
one or more beam generation devices configured to generate one or more particle beams of varying beam intensity, wherein each of the one or more particle beams covers an area of the targeted tissue with varying beam intensity according to a treatment pattern of desired radiation dose distribution;
one or more accelerators configured for accelerating the one or more particle beams of varying beam intensity; and
one or more beam steering devices configured for steering the one or more particle beams of varying beam intensity to the targeted tissue from one or more directions.

56. The system of claim 55, wherein the system is configured such that the one or more particle beams of varying beam intensity comprises an array of beamlets of varying intensity.

57. The system of claim 56, wherein the system is configured such that the array of beamlets of varying intensity is produced by raster scanning individual beamlets of varying intensity from each beam direction or by using a two-dimensional intensity-modulated electron pattern.

58. The system of claim 57, further comprising:
a photo-cathode configured to produce the two-dimensional intensity-modulated electron pattern.

59. The system of claim 57, wherein the system is configured such that the one or more beams of varying intensity comprise multiple beams of varying intensity patterns so that, when delivered from multiple directions, the multiple beams produce a desired three-dimensional dose distribution when summed across the multiple beam directions.

60. The system of claim 55, further comprising:
a controller configured to control delivery of the one or more particle beams to the targeted tissue from the one or more directions thereby irradiating the targeted tissue to deliver an entire treatment dose in less than 10 seconds.

61. A system for treating a patient, comprising:
a photocathode;
a light source configured for projecting or scanning an optical image on the photocathode, the optical image comprising a treatment pattern of varying intensity corresponding to a desired dose distribution across two or more dimensions for treating a targeted tissue of the patient;
a photoelectron gun configured to generate a transverse-modulated electron beam from the optical image produced by the light source on the photocathode;
an accelerator configured to increase the energy level of the transverse-modulated electron beam to a predetermined level; and
a controller capable of controlling delivery of the transverse-modulated electron beam to irradiate the targeted tissue according to the desired dose distribution.

62. The system of claim 61 further comprising:
one or more beam steering devices configured for steering the transverse-modulated electron beam received from the accelerator to the targeted tissue.

63. The system of claim 62 further comprising:
one or more electron beam optics devices configured for maintaining fidelity of the treatment pattern during steering of the transverse-modulated electron beam by the one or more beam steering devices.

64. The system of claim 61 wherein multiple beam steering devices and multiple electron beam optics devices are distributed along the beam path alternating between beam steering devices and electron beam optics devices so as to maintain fidelity of the treatment pattern during steering of the beam with the multiple beam steering devices.

65. The system of claim 62, wherein the one or more beam steering devices comprise bending magnets.

66. The system of claim 55, further comprising:
an electron beam monitoring system disposed along a beam line of the respective beam between the one or more beam steering devices and the target and configured to monitor and/or verify the treatment pattern of the steered transverse-modulating beam before delivery to the targeted tissue.

67. The system of claim 61 further comprising:
a controller capable of controlling a length of time that the transverse-modulated electron beam irradiates the targeted tissue in delivering an entire treatment dose, the length of time being less than 10 seconds.

68. The system of claim 61 wherein the light source is a laser.

69. The system of claim 61, wherein the optical image comprises an intensity pattern corresponding to a dose distribution planned for delivery to the targeted tissue based on a given shape of the targeted tissue.

70. A method of treating a patient, the method comprising:
projecting or scanning an optical image on a photocathode with a light source, the optical image comprising a treatment pattern of varying intensity corresponding to a desired dose distribution across two or more dimensions for treatment of a targeted tissue of the patient;
generating a transverse-modulated electron beam from the optical image produced on the photocathode;
accelerating the transverse-modulated electron beam to increase the energy level of the beam to a predetermined level; and
delivering the beam to the targeted tissue for a predetermined length of time from a first direction so as to irradiate the targeted tissue according to the desired dose distribution.

71. The method of claim 70, further comprising:
steering the beam accelerated to the predetermined level with one or more beam steering devices; and
maintaining fidelity of the treatment pattern of the accelerated beam during steering using one or more beam optics devices.

72. The method of 70 further comprising:
generating one or more additional transverse-modulated particle beams from one or more additional optical images projected or scanned on one or more additional photocathodes;
accelerating the one or more additional transverse-modulated electron beam to increase the energy level of the beam to a predetermined level; and
delivering the beam to the targeted tissue for a predetermined length of time from one or more different directions so as to irradiate the targeted tissue according to the desired dose distribution.

73. The method of 72 further comprising:
steering the one or more additional beams with the one or more beam steering devices; and
maintaining fidelity of the treatment pattern of each of the one or more additional beams during steering with the one or more additional beam optics devices.

74. A method of treating a targeted tissue in a patient, the method comprising:
producing a first transverse-modulated electron beam in a first 2-dimensional intensity pattern;
accelerating and steering the beam in the first 2-dimensional intensity pattern to the targeted tissue from a first direction to irradiate the targeted tissue according to the first 2-dimensional pattern;
producing one or more additional transverse-modulated electron beams in one or more additional 2-dimensional intensity patterns different from the first 2-dimensional intensity pattern; and
accelerating and steering the one or more additional beams to irradiate the targeted tissue according to the one or more additional 2-dimensional intensity patterns from one or more directions different than the first direction, wherein summing the first 2-dimensional intensity pattern and the one or more additional 2-dimensional patterns across the first direction and the one or more additional directions corresponds to a desired 3-dimensional dose distribution suitable for treatment of the targeted tissue.

* * * * *